(12) United States Patent
Nagahama et al.

(10) Patent No.: US 12,187,664 B2
(45) Date of Patent: *Jan. 7, 2025

(54) HIGH PURITY 2-NAPHTHYLACETONITRILE AND METHOD FOR PRODUCING SAME

(71) Applicant: API CORPORATION, Fukuoka (JP)

(72) Inventors: Masaki Nagahama, Chiyoda (JP); Daiki Okado, Chiyoda (JP); Hirotsugu Taniike, Chiyoda (JP)

(73) Assignee: API CORPORATION, Chikujo-gun (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/190,244

(22) Filed: Mar. 27, 2023

(65) Prior Publication Data

US 2023/0227400 A1 Jul. 20, 2023

Related U.S. Application Data

(63) Continuation of application No. 17/295,222, filed as application No. PCT/JP2020/040413 on Oct. 28, 2020, now Pat. No. 11,643,386.

(30) Foreign Application Priority Data

Oct. 29, 2019 (JP) ................................. 2019-196782

(51) Int. Cl.
  *C07C 253/22* (2006.01)
  *C07C 255/33* (2006.01)

(52) U.S. Cl.
  CPC .......... *C07C 253/22* (2013.01); *C07C 255/33* (2013.01)

(58) Field of Classification Search
  None
  See application file for complete search history.

(56) References Cited

U.S. PATENT DOCUMENTS

| 11,643,386 B2* | 5/2023 | Nagahama | ............ | C07C 255/33 |
| | | | | 558/313 |
| 2007/0203111 A1 | 8/2007 | Shao et al. | | |
| 2021/0078940 A1* | 3/2021 | Nagahama | ............. | C07C 51/06 |

FOREIGN PATENT DOCUMENTS

| CN | 112041298 A | 12/2020 |
| JP | 61-268650 A | 11/1986 |
| JP | 2009-531277 A | 9/2009 |
| JP | WO 2019/208807 A1 | 10/2019 |
| WO | WO 2007/016155 A2 | 2/2007 |
| WO | WO 2015/089111 A1 | 6/2015 |
| WO | WO 2015/102826 A1 | 7/2015 |

OTHER PUBLICATIONS

International Search Report and Written Opinion issued Dec. 15, 2020 in PCT/JP2020/040413, filed Oct. 28, 2020, citing documents AA, AK-AM and AT-AY therein, 3 pages.
Wu, G., et al., "Synthesis of α-Aryl Esters and Nitriles: Deaminative Coupling of α-Aminoesters and α-Aminoacetonitriles with Arylboronic Acids", Angew. Chem. Int. Ed., vol. 53, No. 39, 2014, p. 10510-10514.
Kangai, C.O., et al., "Controlled conversion of phenylacetic acids to phenylacetonitriles or benzonitriles using bis(2-methoxyethyl)aminosulfur trifluoride", ScienceDirect, Tetrahedron Letters, vol. 49, No. 5, 2008, pp. 914-918.
Huber, V.J., et al., "Preparation of Nitriles from Carboxylic Acids: A New, Synthetically Useful Example of the Smiles Rearrangement", Tetrahedron, vol. 54, No. 32, 1998, pp. 9281-9288.
Price, C.C., et al., "The Preparation of Several Chlorinated 1-vinylnaphthalenes". J. Org. Chem., vol. 14, 1949, pp. 111-117.
Alam, M. M. et al., "A Facile Synthesis of Phenylacetic Acids via Willgerodt-Kindler Reaction Under PTO Condition", Synthetic Communications, vol. 33, No. 1, 2003, pp. 59-63.
Hulkenberg, A. et al., "An Efficient One-Pot Synthesis of Nitriles From Acid Chlorides", Tetrahedron Letters, vol. 23, No. 14, 1982, pp. 1505-1508.
Sasiambarrena L. D. et al., "Intramolecular sulfonylamidomethylation of 2-(2-naphthyl) and 2-(1-naphthyl)ethanesulfonamides: synthesis of new class of naphthosultams", Tetrahedron Letters, vol. 56, 2015, pp. 2054-2058.
Combined Chinese Office Action and Search Report issued Nov. 2, 2021 in Chinese Patent Application No. 202080011042.9 (with English translation), citing documents AO and AX therein, 19 pages.
Melvin S. Newman, "New Syntheses of Picene", Journal of Organic Chemistry, vol. 9, No. 6, pp. 518-528.
Extended European Search Report as received in the corresponding EP Patent Application No. 20882467.2 dated Apr. 13, 2022, AW citing 11 pages.
Kangani Cyrous O et al., "Supporting Information Controlled conversion of phenylacetic acids to phenylacetonitriles or benzonitriles using bis(2-methoxyethyl)aminosulfur trifluoride", Tetrahedron Letters, 2008, pp. S1-S22, Retrieved from Internet: URL:https://ars.els-cdn.com/content/image/1-s2.0-S0040403907022885-mmc1.pdf.
Office Action issued Feb. 17, 2023, in corresponding European Patent Application No. 20 882 467.2, 6 pages.

(Continued)

*Primary Examiner* — Samantha L Shterengarts
*Assistant Examiner* — Jed A Kucharczk
(74) *Attorney, Agent, or Firm* — Oblon, McClelland, Maier & Neustadt, L.L.P.

(57) ABSTRACT

High purity 2-naphthylacetonitrile with fewer impurities that is useful as a starting material or intermediate for the synthesis of various pharmaceutical products, agricultural chemicals, and chemical products, and a production method thereof. A high purity 2-naphthylacetonitrile having an HPLC purity of 2-naphthylacetonitrile of not less than 95 area %, and containing naphthalene compounds represented by the formulas (a)-(j) at a content of a predetermined area % or below. A method for producing high purity 2-naphthylacetonitrile.

8 Claims, 1 Drawing Sheet

(56) References Cited

OTHER PUBLICATIONS

Office Action issued Jun. 9, 2023, in corresponding Canadian Patent Application No. 3,159,756, 4 pages.
Office Action issued Sep. 16, 2022, in corresponding Indian Patent Application No. 202217029759, (with English Translation), 6 pages.
Combined Chinese Office Action and Search Report issued Jun. 24, 2022, in corresponding Chinese Patent Application No. 202080011042.9 (with English Translation), 19 pages.
Office Action issued Dec. 28, 2022, in corresponding Chinese Patent Application No. 202080011042.9, (with English Translation), 13 pages.
Canadian Office Action issued Jun. 13, 2024 in Canadian Patent Application No. 3,159,756, 3 pages.
European Office Action issued Jun. 25, 2024 in European Patent Application No. 20882467.2, 5 pages.
Notification of Reexamination in the corresponding Chinese Patent Application No. 202080011042.9 issued Sep. 12. 2024 (with English translation).

* cited by examiner

HIGH PURITY 2-NAPHTHYLACETONITRILE AND METHOD FOR PRODUCING SAME

The present application is a continuation of U.S. application Ser. No. 17/295,222 filed May 19, 2021, allowed, which is a national stage of international application PCT/JP2020/040413 filed on Oct. 28, 2020 and claims the benefit of the filing date of Japanese Application No. 2019/196782 filed on Oct. 29, 2019, the contents of which are incorporated by reference in full herein.

TECHNICAL FIELD

The present invention relates to high purity 2-naphthylacetonitrile useful as a starting material or intermediate for the synthesis of various pharmaceutical products, agricultural chemicals, chemical products and the like, and a production method thereof.

BACKGROUND ART

2-Naphthylacetonitrile is useful as a starting material for synthesis, or an intermediate for synthesis of various pharmaceutical products, agricultural chemicals, chemical products and the like. In addition, an aromatic nitrile compound having a chemical structure similar to that of 2-naphthylacetonitrile is expected to be usable as a starting material for synthesis, or an intermediate for synthesis of various pharmaceutical products, agricultural chemicals, and chemical products.

For example, 2-naphthylacetonitrile is useful as a starting material for synthesis, or an intermediate for synthesis of pharmaceutical products such as pharmaceutical products used for the prophylaxis, treatment and the like of depression (e.g., major depressive disorder, bipolar disease), fibromyalgia, pain (e.g., neuropathic pain), sleep disorder, attention deficit disorder (ADD), attention deficit hyperactivity disorder (ADHD), restless legs syndrome, schizophrenia, anxiety, obsessive-compulsive disorder, post-traumatic stress disorder, seasonal affective disorder (SAD), premenstrual dystonia, CNS diseases such as neurodegenerative disease (e.g., Parkinson's disease, Alzheimer's disease) and the like, diseases relating to urinary incontinence and irritable bowel syndrome (IBS), diabetes and the like, erythropoietin (EPO) inducer, calcium antagonist, histamine receptor antagonist, tachykinin receptor antagonist, 12-lipoxygenase inhibitor, protein kinase C (PKC) inhibitor, PDE IV inhibitor and the like.

2-Naphthylacetonitrile can be particularly preferably used as a starting material/intermediate for producing (1R,5S)-1-(naphthalen-2-yl)-3-azabicyclo[3.1.0]hexane which is a pharmaceutical product described in patent document 1, patent document 2, patent document 3 and the like.

As a production method of 2-naphthylacetonitrile, a method including brominating 2-methylnaphthalene to give 2-(bromomethyl)naphthalene, and reacting same with potassium cyanide (non-patent document 1) is known.

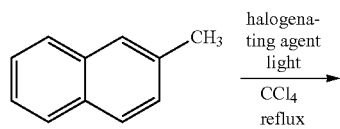

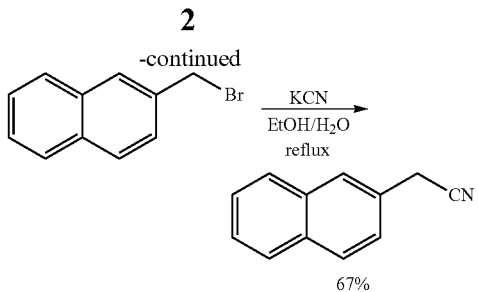

However, this method is not preferable as an industrial production method since the yield is low, many by-products are generated by bromination, highly toxic compounds such as carbon tetrachloride, potassium cyanide and the like are used, and the like.

Furthermore, a method for synthesizing a nitrile compound from aromatic carboxylic acid, aromatic carboxylic acid derivative and the like has been reported (non-patent document 2).

Non-patent document 2 describes a method including dissolving carboxylic acid halide having various structures such as aromatic ring and the like and sulfamide in sulfolane, and reacting and converting same to a nitrile compound.

In the method of non-patent document 2, however, some substrates show low yields, and further improvements are desired as an industrial production method.

A method for synthesizing aromatic carboxylic acid and aromatic thioamide from aromatic ketone by Willgerodt reaction has been reported in non-patent document 3.

However, these methods require further improvement as industrial production methods since the yield is not sufficient and the resulting aromatic carboxylic acid and the like are considered to contain much sulfur due to the use of sulfur in Willgerodt reaction.

In addition, 2-naphthylacetonitrile obtained by these methods is considered to contain several percents of by-products such as sulfur, amide compound, thioamide compound and the like, inferring from these production methods and the yields thereof.

DOCUMENT LIST

Patent Documents patent document 1: WO 2007/016155
patent document 2: WO 2015/089111
patent document 3: WO 2015/102826

Non-Patent Documents non-patent document 1: Tetrahedron Letters 56 (2015) 2054-2058
non-patent document 2: Tetrahedron Letters, Vol. 23, No. 14, pp. 1505-1508, 1982
non-patent document 3: Synthetic Communications, Vol. 33, No. 1, pp. 59-63, 2003

SUMMARY OF INVENTION

Technical Problem

The present invention provides a method for producing high purity 2-naphthylacetonitrile which has fewer impurities, and can be produced safely and highly efficiently on an industrial scale at a low cost.

Solution to Problem

In an attempt to solve the above-mentioned problems, the present inventors found production of aromatic carboxylic acid compound by Willgerodt rearrangement using comparatively economical and general aromatic ketone compounds such as 2'-acetonaphthone and the like, and further, a method for producing a highly pure aromatic nitrile compound such as 2-naphthylacetonitrile and the like in a high yield from the aromatic carboxylic acid compound (International Application No. PCT/JP2019/018065).

Generally, the starting materials and intermediates for synthesizing pharmaceutical products are required to have high purity so that unexpected side effects will not be caused by impurities contained therein. As the impurity, by-products resulting from the production of these can be mentioned. By-products may be removed during purification and production process of the target drug. However, when pharmaceutical products are industrially produced in large amounts, further reduction of production costs and purification costs is desired to achieve stable supply, suppression of price and the like of the pharmaceutical products. Thus, highly pure starting materials and intermediates containing less impurities are desired for synthesizing pharmaceutical products.

The present inventors have studied and found that 2-naphthylacetonitrile obtained by the production method described in the aforementioned international application has a lower content of by-products than by conventionally known methods, and reached the present invention.

The present inventors have further studied the production method.

That is, the gist of the present invention is as follows.

[1] A high purity 2-naphthylacetonitrile having an HPLC purity of 2-naphthylacetonitrile of not less than 95 area %, comprising one or more kinds selected from the naphthalene compounds represented by the following formulas (a)-(j) as impurities, wherein a content of each naphthalene compound is as follows:

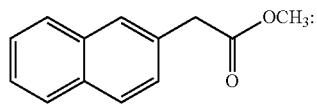
(a)

not more than 0.3 area %

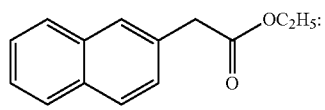
(b)

not more than 0.1 area %

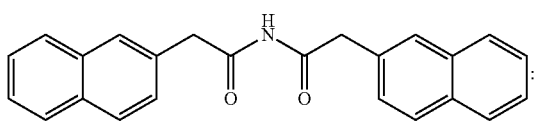
(c)

not more than 1 area %

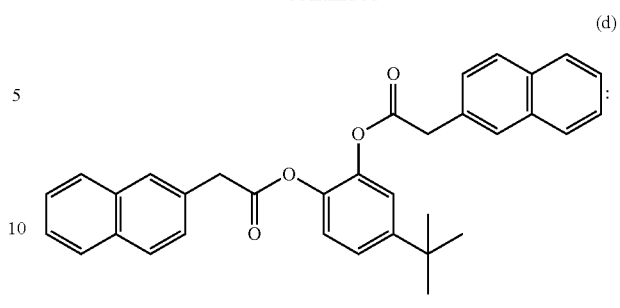
(d)

not more than 0.1 area %

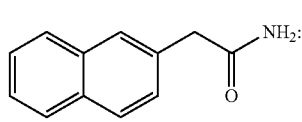
(e)

not more than 0.05 area %

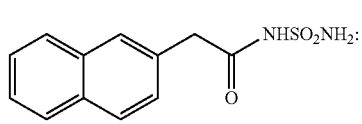
(f)

not more than 0.05 area %

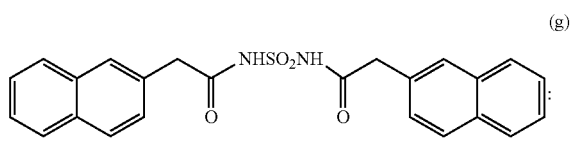
(g)

not more than 0.1 area %

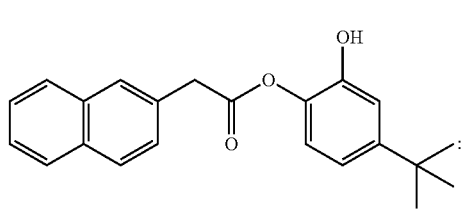
(h)

not more than 0.05 area %

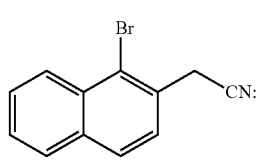
(i)

not more than 0.05 area %

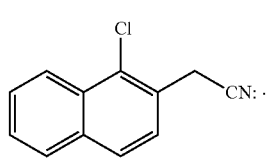
(j)

not more than 0.05 area %

[2] The high purity 2-naphthylacetonitrile of [1], comprising one or more kinds selected from the naphthalene compounds represented by the following formulas (a)-(d) as impurities, wherein the content of each naphthalene compound is as follows:

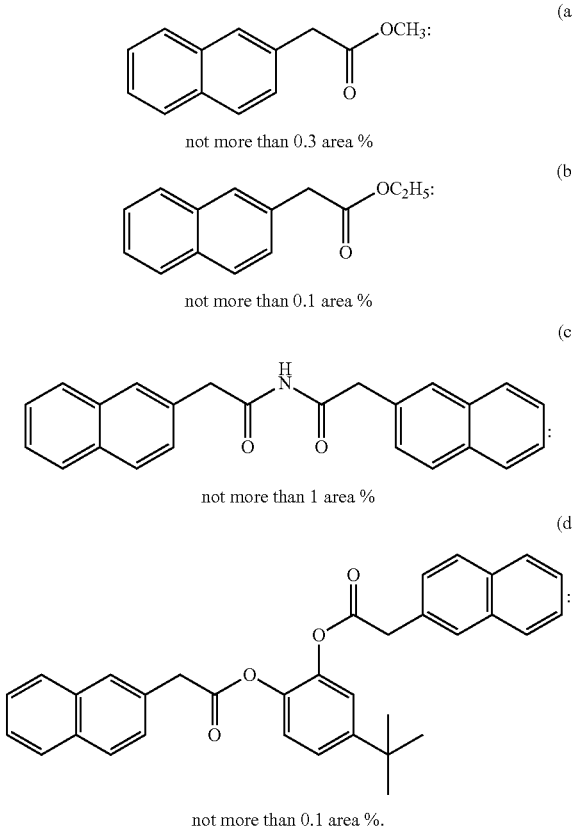

(a) not more than 0.3 area %

(b) not more than 0.1 area %

(c) not more than 1 area %

(d) not more than 0.1 area %.

[3] The high purity 2-naphthylacetonitrile of [1], comprising the naphthalene compound represented by the following formula (c) as impurity, wherein the content of the naphthalene compound represented by the following formula (c) is not more than 1 area %:

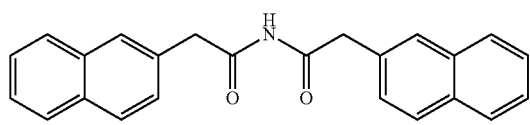

(C)

[4] A method for producing a high purity 2-naphthylacetonitrile, comprising mixing a reaction starting material 1 comprising an acid halide compound represented by the following formula (5)

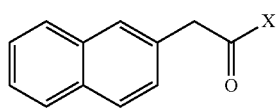

(5)

wherein, in the formula (5), X is a halogen atom, and a first organic solvent, and a reaction starting material 2 comprising sulfamide and a second organic solvent at 15° C.-90° C., raising the temperature and reacting the mixture at 80° C.-180° C. to give 2-naphthylacetonitrile.

[5] The production method of [4], wherein the reaction starting material 1 is added to the reaction starting material 2 at 15° C.-90° C., the temperature is raised, and the mixture is reacted at 80° C.-180° C.

[6] The production method of [5], wherein the reaction starting material 1 is added to the reaction starting material 2 such that the amount of the acid halide compound represented by the aforementioned formula (5)

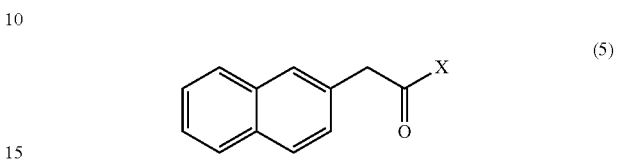

(5)

is not less than 0.0027 mol/min per 1 mol of sulfamide.

[7] The production method of any one of [4] to [6], wherein the reaction starting material 1 is obtained by mixing 2-naphthylacetic acid, a halogenating agent and the first organic solvent in the presence of a catalyst where necessary.

[8] A method for producing high purity 2-naphthylacetonitrile, comprising the following step 1 and step 2:

Step 1:
a step of subjecting 2'-acetonaphthone to a Willgerodt reaction in the presence of an additive where necessary, hydrolyzing the obtained amide compound, and liberating 2-naphthylacetic acid to give 2-naphthylacetic acid;

Step 2:
a step of mixing and reacting a reaction starting material 1 comprising the 2-naphthylacetic acid obtained in step 1, a halogenating agent and a first organic solvent, and a reaction starting material 2 comprising sulfamide and a second organic solvent to give 2-naphthylacetonitrile.

[9] The production method of any one of [4] to [7], wherein the first organic solvent is a hydrocarbon solvent, an amide solvent, a sulfone solvent or a mixed solvent thereof, and the second organic solvent is a sulfone solvent.

In addition, the present invention relates to the following.

[1A] A high purity 2-naphthylacetonitrile having an HPLC purity of 2-naphthylacetonitrile of not less than 95 area %, and comprising naphthalene compounds represented by the following formulas (a)-(i) at the following contents:

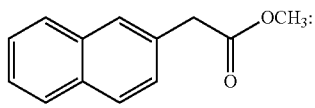

(a) not more than 0.3 area %

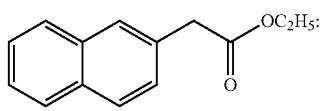

(b) not more than 0.1 area %

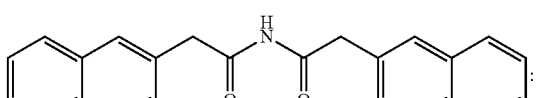

(c) not more than 1 area %

(d)

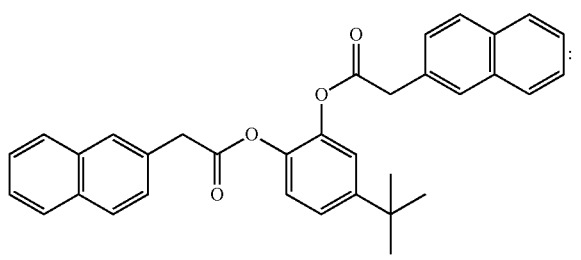

not more than 0.1 area %

(e)

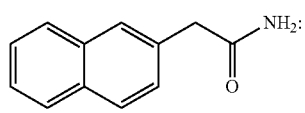

not more than 0.05 area %

(f)

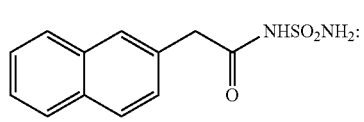

not more than 0.05 area %

(g)

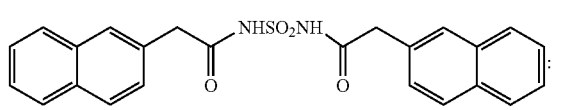

not more than 0.1 area %

(h)

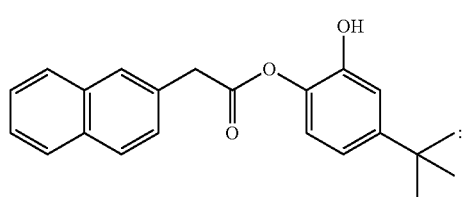

not more than 0.05 area %

(i)

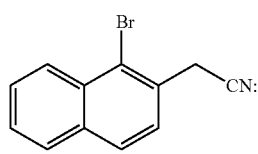

not more than 0.05 area %

[2A] A method for producing a high purity 2-naphthylacetonitrile, comprising the following step 1A and step 2A:

Step 1A:

a step of subjecting 2'-acetonaphthone to a Willgerodt reaction in the presence of an additive where necessary, hydrolyzing the obtained amide compound, and neutralizing same to give 2-naphthylacetic acid;

Step 2A:

a step of reacting the 2-naphthylacetic acid obtained in step 1A, a halogenating agent and a compound represented by the following formula (7)

$$R^1SO_2R^2 \qquad (7)$$

wherein $R^1$ and $R^2$ are each independently a chlorine atom, a hydroxyl group, an amino group, an isocyanate group or a p-tolyl group, in the presence of a catalyst as necessary in an organic solvent to give 2-naphthylacetonitrile.

[3A] The production method of [2A], wherein the aforementioned step 2A is a step of mixing and reacting a reaction starting material 1 which is a mixture of the 2-naphthylacetic acid obtained in step 1A, a halogenating agent, a first organic solvent and, where necessary, a catalyst, with a reaction starting material 2 which is a mixture of a compound represented by the aforementioned formula (7) and a second organic solvent to give 2-naphthylacetonitrile.

[4A] The production method of [3A], wherein the first organic solvent is a hydrocarbon solvent, a sulfone solvent or a mixture of these, and the second organic solvent is a sulfone solvent.

[5A] The production method of [3A], wherein the aforementioned step 2A is a step of mixing a reaction starting material 1 which is a mixture of the 2-naphthylacetic acid obtained in step 1A, a halogenating agent, a first organic solvent and, where necessary, a catalyst, with a reaction starting material 2 which is a mixture of a compound represented by the aforementioned formula (7) and a second organic solvent at 15° C.-90° C., raising the temperature and reacting the mixture at 80° C.-180° C. to give 2-naphthylacetonitrile.

[6A] The production method of [3A], wherein the aforementioned step 2A is a step of adding a reaction starting material 1 which is a mixture of the 2-naphthylacetic acid obtained in step 1A, a halogenating agent, a first organic solvent and, where necessary, a catalyst, to a reaction starting material 2 which is a mixture of a compound represented by the aforementioned formula (7) and a second organic solvent and reacting the mixture to give 2-naphthylacetonitrile, wherein the reaction starting material 1 is added to the reaction starting material 2 such that the amount of an acid halide compound represented by the following formula (5)

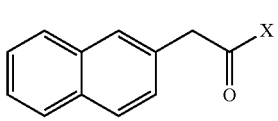 (5)

wherein, in the formula (5), X is a halogen atom, contained in the reaction starting material 1 is not less than 0.0027 mol/min per 1 mol of the compound represented by the aforementioned formula (7) contained in the reaction starting material 2.

[7A] The production method of [2A], wherein, after the aforementioned hydrolysis in the aforementioned step 1A, the reaction product obtained by the hydrolysis is contacted with a hydrocarbon solvent; a hydrocarbon solvent is present during the aforementioned neutralization; or the reaction product obtained by the aforementioned neutralization is contacted with a hydrocarbon solvent.

Advantageous Effects of Invention

According to the present invention, high purity 2-naphthylacetonitrile with less impurity which is useful as a starting material or intermediate for the synthesis of various pharmaceutical products, agricultural chemicals, and chemical products, particularly a starting material or intermediate for the synthesis of pharmaceutical products, can be provided. In addition, a production method capable of producing high purity 2-naphthylacetonitrile safely, highly efficiently, industrially in a large amount at a low cost can be provided. Furthermore, using the 2-naphthylacetonitrile of the present invention, pharmaceutical products such as (1R,5S)-1-(naphthalen-2-yl)-3-azabicyclo[3.1.0]hexane and the like can be produced industrially in a large amount at a low cost.

DESCRIPTION OF EMBODIMENTS

Figure 1:
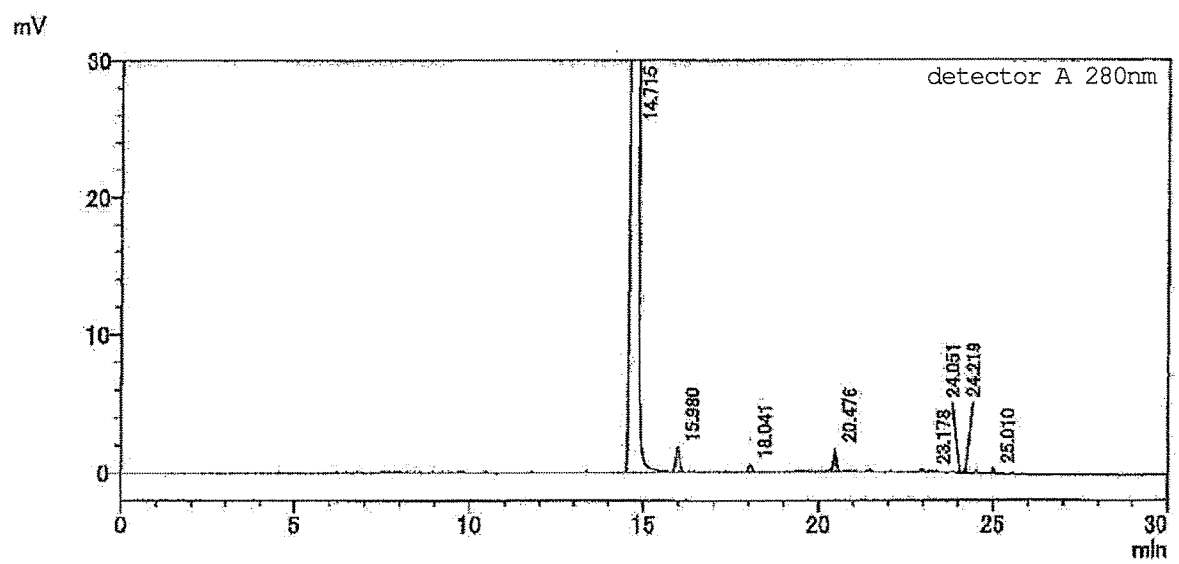
FIG. 1 shows the HPLC analysis results of 2-naphthylacetonitrile obtained in Example 1.

The present invention is described in detail below.

High Purity 2-Naphthylacetonitrile of the Present Invention

The high purity 2-naphthylacetonitrile of the present invention shows lower contents of specific by-products (impurities) than before. To be specific, an HPLC purity of 2-naphthylacetonitrile is not less than 95 area %, and the contents of the naphthalene compounds represented by the following formulas (a)-(j) are as shown in Table 1.

TABLE 1

| | | |
|---|---|---|
| (a) | 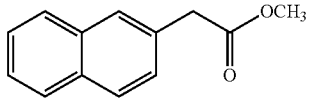 [SMILES: COC(=O)Cc1ccc2ccccc2c1] | not more than 0.3 area % |
| (b) | 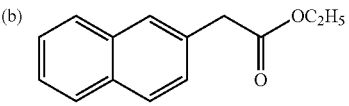 | not more than 0.1 area % |
| (c) | 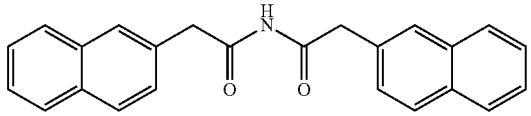 [SMILES: O=C(Cc1ccc2ccccc2c1)NC(=O)Cc1ccc2ccccc2c1] | not more than 1 area % |
| (d) | 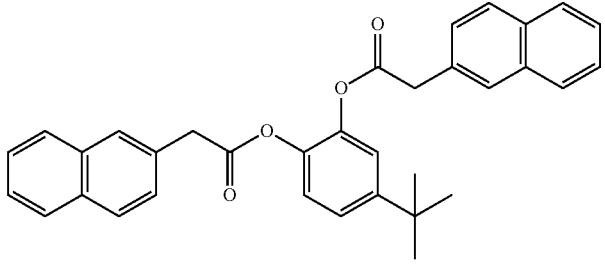 [SMILES: CC(C)(C)c1ccc(OC(=O)Cc2ccc3ccccc3c2)c(OC(=O)Cc2ccc3ccccc3c2)c1] | not more than 0.1 area % |
| (e) | 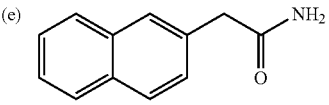 | not more than 0.05 area % |
| (f) | 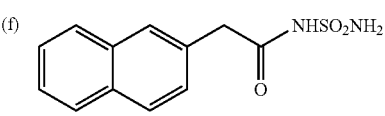 | not more than 0.05 area % |
| (g) | 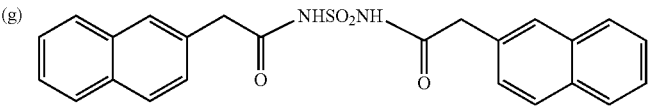 | not more than 0.1 area % |
| (h) | 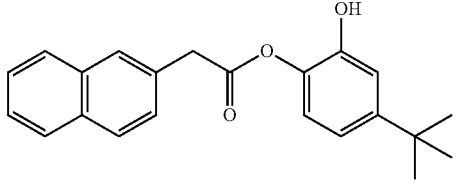 [SMILES: CC(C)(C)c1ccc(OC(=O)Cc2ccc3ccccc3c2)c(O)c1] | not more than 0.05 area % |

TABLE 1-continued

| | | |
|---|---|---|
| (i) | ![1-bromo-2-naphthylacetonitrile structure] | not more than 0.05 area % |
| (j) | ![1-chloro-2-naphthylacetonitrile structure] | not more than 0.05 area % |

The compounds represented by the above-mentioned formulas (a), (b), (c), (d) and (h) are impurities that are difficult to remove by purification operations such as solid-liquid separation by crystallization, column purification and the like, and it is preferable to suppress the production amount thereof from the aspects of quality and purification cost.

The compounds represented by the above-mentioned formulas (e), (f), (g), (i) and (j) have high reactivity and sometimes cause side reactions. Thus, it is preferable to prevent them from remaining in 2-naphthylacetonitrile.

The HPLC purity of the high purity 2-naphthylacetonitrile of the present invention is preferably not less than 97 area %, more preferably not less than 98 area %, particularly preferably not less than 99 area %.

The content of the naphthalene compound represented by the above-mentioned formula (a) is preferably not more than 0.25 area %, more preferably not more than 0.2 area %, further preferably not more than 0.15 area %, particularly preferably not more than 0.1 area %.

The content of each of the naphthalene compounds represented by the above-mentioned formulas (b) and (d) is preferably not more than 0.08 area %, more preferably not more than 0.05 area %, further preferably not more than 0.03 area %, particularly preferably not more than 0.01 area %.

The content of the naphthalene compound represented by the above-mentioned formula (c) is preferably not more than 0.8 area %, more preferably not more than 0.5 area %, further preferably not more than 0.3 area %, particularly preferably not more than 0.1 area %.

The content of each of the naphthalene compounds represented by the above-mentioned formulas (e), (f) and (h) is preferably not more than 0.03 area %, more preferably not more than 0.02 area %, further preferably not more than 0.01 area %, particularly preferably not more than 0.005 area %.

The content of the naphthalene compound represented by the above-mentioned formula (g) is preferably not more than 0.08 area %, more preferably not more than 0.05 area %, further preferably not more than 0.03 area %, particularly preferably not more than 0.01 area %.

The content of each of the naphthalene compounds represented by the above-mentioned formulas (i) and (j) is preferably not more than 0.03 area %, more preferably not more than 0.02 area %, further preferably not more than 0.01 area %, particularly preferably 0 area %.

The content of the naphthalene compound represented by the following formula is preferably not more than 0.08 area %, more preferably not more than 0.05 area %, further preferably not more than 0.03 area %, particularly preferably not more than 0.01 area %:

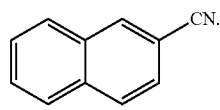 [SMILES: N#Cc1ccc2ccccc2c1]

The high purity 2-naphthylacetonitrile of the present invention has a small content of impurities and can be sufficiently used as it is as a starting material or intermediate for the synthesis of pharmaceutical products even without a purification operation or the like. Therefore, it is useful as a starting material or intermediate for the synthesis of pharmaceutical products.

The production method of the present invention to be described later can suppress production of the naphthalene compound represented by the above-mentioned formula (c) which has the highest content among the impurities in the high purity 2-naphthylacetonitrile of the present invention.

The relative retention time (RRT) of the naphthalene compounds represented by the above-mentioned formulas (a)-(h) is as shown in Table 2. The relative retention time may vary by about ±0.05 due to the HPLC measurement conditions.

TABLE 2

| naphthalene compound | RRT |
|---|---|
| 2-naphthylacetonitrile | 1.00 |
| (a) | 1.08 |
| (b) | 1.22 |
| (c) | 1.35 |
| (d) | 1.57 |
| (e) | 0.49 |
| (f) | 0.58 |
| (g) | 1.22 |
| (h) | 1.40 |

In the present invention, the purity and the content of impurity of 2-naphthylacetonitrile can be measured by the peak area ratio in high performance liquid chromatography (HPLC) which is a method well known in the field of analysis chemistry. The measurement conditions of HPLC can be appropriately selected, and the conditions shown below are preferred.

analysis instrument: HPLC (1200 series) manufactured by Agilent column: Zorbax Eclipse Plus Phenyl-Hexyl, 5 μm, 250 mm×4.6 mm mobile phase A: 0.1 volume % trifluoroacetic acid aqueous solution mobile phase B: acetonitrile gradient: 0 min (B:30%)—15 min (B:60%)—20 min (B:95%)—30 min (B:95%)
flow rate: 1.0 mL/min
injection volume: 5 μL
detection wavelength: 280 nm
column temperature: 40° C.

The color tone of the high purity 2-naphthylacetonitrile of the present invention is white to brown, preferably white to pale brown. The water content of the high purity 2-naphthylacetonitrile of the present invention is generally not more than 2.0 wt %, preferably not more than 1.5 wt %, more preferably not more than 1.0 wt %.

In the production process of the high purity 2-naphthylacetonitrile of the present invention, sulfur and an organic solvent are used, but the contents thereof are also small. The sulfur content of the high purity 2-naphthylacetonitrile of the present invention is generally not more than 0.5 area %, preferably not more than 0.3 area %, more preferably not more than 0.1 area %, particularly preferably not more than 0.05 area %. The content of an organic solvent such as sulfolane, toluene or the like is generally not more than 0.5 wt %, preferably not more than 0.3 wt %, more preferably not more than 0.1 wt %, particularly preferably not more than 0.05 wt %.

As described above, the high purity 2-naphthylacetonitrile of the present invention has high HPLC purity of not less than 95 area %, more preferably not less than 98 area %, and a lower impurity content than that of 2-naphthylacetonitrile produced by a conventionally-known method. Thus, when it is used as a starting material or intermediate for the synthesis of pharmaceutical products, high reactivity is expected. In addition, the high purity 2-naphthylacetonitrile of the present invention is excellent in solubility, and shows high dissolution rates in organic solvents. Therefore, the high purity 2-naphthylacetonitrile of the present invention is useful as a starting material or intermediate for the synthesis of pharmaceutical products to be produced industrially in large amounts.

Production Method of the High Purity 2-Naphthylacetonitrile of the Present Invention The production method of the high purity 2-naphthylacetonitrile of the present invention includes a step of obtaining 2-naphthylacetic acid represented by the following formula (3) from 2'-acetonaphthone represented by the following formula (2) (step 1), and a step of obtaining 2-naphthylacetonitrile represented by the following formula (1) from 2-naphthylacetic acid (step 2).

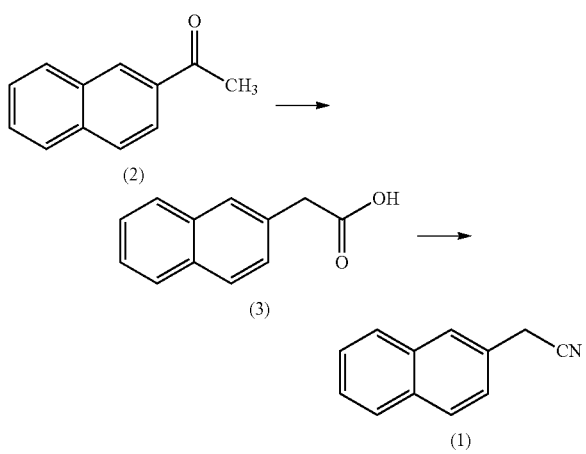

<<Step 1>>

In step 1, 2'-acetonaphthone represented by the formula (2) is subjected to a Willgerodt reaction, and the obtained compound is hydrolyzed to give 2-naphthylacetic acid represented by the formula (3).

In the present specification, the Willgerodt reaction means a Willgerodt reaction and a Willgerodt-Kindler reaction.

[Willgerodt Reaction]

The Willgerodt reaction can be performed by reacting 2'-acetonaphthone with a sulfur compound such as sodium sulfide ($Na_2S \cdot 9H_2O$), ammonium sulfide (($NH_4$)$_2$S) and the like under heating.

[Willgerodt-Kindler Reaction]

The Willgerodt-Kindler reaction can be performed by reacting 2'-acetonaphthone with sulfur and secondary amine such as dialkylamine, morpholine and the like under heating.

<Starting Materials>

(2'-Acetonaphthone)

As 2'-acetonaphthone, a commercially available one may also be used, and one obtained by a known method may also be used.

(Sulfur Compound)

As the sulfur compound, one kind may be used alone, or two or more kinds may be used in any combination and ratio.

The amount of the sulfur compound to be used is not particularly limited as long as it is an amount effective for the Willgerodt reaction of 2'-acetonaphthone. The amount of the sulfur compound to be used is generally 1 mol-5 mol, preferably 1 mol-3 mol, per 1 mol of 2'-acetonaphthone.

(Sulfur)

The amount of the sulfur to be used is not particularly limited as long as it is an amount effective for reaction, and is generally 1 mol-5 mol, preferably 1 mol-3 mol, per 1 mol of 2'-acetonaphthone.

(Secondary Amine)

The secondary amine for industrial production is preferably morpholine since reaction without solvent can be performed efficiently.

The amount of the secondary amine to be used is not particularly limited as long as it is an amount effective for reaction. The amount of the secondary amine to be used is generally 1 mol-6 mol, preferably 2 mol-4 mol, per 1 mol of 2'-acetonaphthone.

(Solvent)

Step 1 can be performed without solvent or in an organic solvent inert to the reaction.

Examples of the organic solvent include dioxane, N,N-dimethylformamide and the like. Of these organic solvents, one kind may be used alone, or two or more kinds may be used in any combination and ratio. When the reaction is performed using a sulfur compound, the reaction can also be performed in the presence of an aqueous solvent such as water and the like.

(Additive)

In step 1, an additive may also be used as necessary.

Examples of the additive include dehydrating agents such as zeolite, molecular sieves, magnesium sulfate, sodium sulfate and the like. As the dehydrating agent, one kind may be used alone, or two or more kinds may be used in any combination and ratio. The reaction can proceed efficiently by controlling the amount of water in the reaction system to a low level.

The amount of the dehydrating agent to be used is not particularly limited as long as dehydration proceeds efficiently. It is generally 1 mol-5 mol, preferably 1.5 mol-4 mol, per 1 mol of 2'-acetonaphthone.

Examples of the additive include organic acids such as p-toluenesulfonic acid, methanesulfonic acid, oxalic acid, trifluoroacetic acid and the like. As the organic acid, one kind may be used alone, or two or more kinds may be used in any combination and ratio. As the organic acid, p-toluenesulfonic acid or methanesulfonic acid is particularly preferable. Using these additives, production of by-products, particularly a ketothioamide compound represented by the following formula

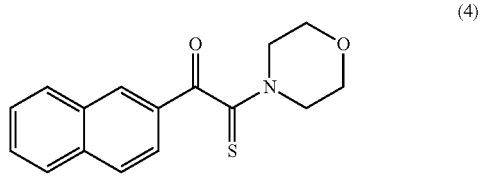 [SMILES: O=C(C(=S)N1CCOCC1)c1ccc2ccccc2c1]

(4)

is suppressed, and the reaction can proceed efficiently.

The amount of the organic acid to be used is generally 0.01 mol-5 mol, preferably 0.05 mol-3 mol, per 1 mol of 2'-acetonaphthone.

To control the amount of water in the reaction system to a low level, the reaction may be performed while dehydrating by distillation.

<Reaction Conditions>
(Reaction Method)

While the production method of the present invention may be of a batch type or a continuous type, it is generally of a batch type.

(Reaction Temperature)

The reaction temperature is generally 90° C.-150° C., preferably 100° C.-140° C., particularly preferably 110° C.-130° C.

(Reaction Pressure)

The reaction is generally performed under normal pressure, but may also be performed under pressurization.

(Reaction Time)

The reaction time can be appropriately determined according to the progress of the reaction and is generally 1 hr-24 hr, preferably 2 hr-12 hr.

<Post-Treatment>
[Hydrolysis]

The compound obtained by the Willgerodt reaction may be subjected to hydrolysis after separation from the reaction system, or may be subjected to the next hydrolysis without separation.

In the present invention, the compound obtained by the Willgerodt reaction may be hydrolyzed with a base.

(Base)

Examples of the base include alkali metal hydroxides such as sodium hydroxide, potassium hydroxide and the like; alkaline earth metal hydroxides such as calcium hydroxide and the like; alkali metal carbonates such as sodium carbonate, potassium carbonate and the like; alkaline earth metal carbonates such as calcium carbonate and the like; alkali metal hydrogen carbonates such as sodium hydrogen carbonate, potassium hydrogen carbonate and the like; alkaline earth metal hydrogen carbonates such as calcium hydrogen carbonate and the like; and alkali metal alkoxides such as sodium methoxide, sodium ethoxide, potassium methoxide, potassium ethoxide and the like. Industrially, it is preferable to use alkali metal hydroxides such as sodium hydroxide, potassium hydroxide and the like because of the cost and availability. As the base, one kind may be used alone, or two or more kinds may be used in any combination and ratio.

The amount of the base to be used is not particularly limited as long as it is an amount effective for hydrolysis of the compound obtained after the Willgerodt reaction. The amount of the base to be used is generally 1 mol-10 mol, preferably 1 mol-5 mol, per 1 mol of the compound obtained after the Willgerodt reaction.

(Solvent)

Hydrolysis may be performed without a solvent or in a solvent such as water and the like. It is preferably performed in a solvent in view of superior stirrability and uniformity.

(Reaction Temperature)

The reaction temperature of hydrolysis is not particularly limited as long as the hydrolysis proceeds. The hydrolysis temperature is generally 80° C.-115° C., preferably 85° C.-110° C.

(Reaction Pressure)

Hydrolysis is generally performed under normal pressure, but may also be performed under pressurization.

[Liberation Reaction]

The 2-naphthylacetic acid represented by the formula (3) can be liberated by reacting a reaction product obtained by hydrolysis (e.g., 2-naphthylacetic acid or a salt thereof) with an acid.

(Acid)

For a liberation reaction of 2-naphthylacetic acid, an acid such as hydrochloric acid, sulfuric acid, hydrobromic acid or the like can be used.

As the acid, one kind may be used alone, or two or more kinds may be used in any combination and ratio. Industrially, hydrochloric acid is preferable because of the reaction efficiency, cost and the like.

The amount of the acid to be used is not particularly limited as long as it is an amount effective for neutralization. The amount of the acid to be used is generally 1 mol-20 mol, preferably 3 mol-10 mol, per 1 mol of the compound obtained by hydrolysis.

<Reaction Conditions>
(pH of Liquid)

The pH of the mixture during the liberation reaction of 2-naphthylacetic acid is generally 0-5, preferably 0-3.

(Reaction Temperature)

The temperature of the liberation reaction is not particularly limited as long as the liberation proceeds. The temperature of the liberation reaction is generally 50° C.-90° C., preferably 60° C.-80° C.

(Reaction Time)

The reaction time is generally 10 min-5 hr, preferably 30 min-2 hr.

(Reaction Pressure)

While the reaction pressure is generally normal pressure, the reaction may also be performed under pressurization.

(Supply Method)

As a supply method, an acid may be supplied to the reaction product obtained by hydrolysis which is placed in a reactor, or an acid is placed in a reactor, and the reaction product obtained by hydrolysis may be supplied, or the reaction product obtained by hydrolysis and an acid may be supplied at the same time.

<Post-Treatment>

2-Naphthylacetic acid can be extracted and recovered using an organic solvent from the reaction product obtained by liberation reaction.

(Organic Solvent)

Examples of the organic solvent include hydrocarbon solvents capable of dissolving 2-naphthylacetic acid. Examples of the hydrocarbon solvent include alicyclic hydrocarbon solvents such as cyclohexane, methylcyclohexane and the like; aromatic hydrocarbon solvents such as benzene, toluene, xylene, mesitylene, ethylbenzene, tert-butylbenzene and the like; and aromatic halogenated hydrocarbon solvents such as trifluoromethylbenzene, nitrobenzene, chlorobenzene, chlorotoluene, bromobenzene and the like. As the hydrocarbon solvent, alicyclic hydrocarbon solvent and aromatic hydrocarbon solvent are preferable, and cyclohexane, toluene and xylene are particularly preferable, from the aspect of cost.

The hydrocarbon solvent may be used alone, or two or more kinds may be used in any combination and ratio.

The amount of the organic solvent to be used is generally 1 volume ratio-20 volume ratio, preferably 1.5 volume ratio-10 volume ratio, particularly preferably 3 volume ratio-5 volume ratio, with respect to 2-naphthylacetic acid.

(Purification Method)

Since sulfur or sulfur compound is used in step 1, the obtained reaction product generally contains several mol % or more of sulfur. Sulfur is an impurity for 2-naphthylacetic acid which is the target product of step 1. When a chemical reaction or the like is performed using the 2-naphthylacetic acid as a starting material, sulfur may decrease the reaction efficiency. Accordingly, it is preferable to remove sulfur as much as possible.

In the present invention, the sulfur content of the 2-naphthylacetic acid obtained in step 1 can be decreased by contacting the reaction product obtained by hydrolysis with a hydrocarbon solvent after the aforementioned hydrolysis, performing the aforementioned liberation in the presence of a hydrocarbon solvent, or contacting the reaction product obtained by the aforementioned liberation with a hydrocarbon solvent. Water, an aqueous solution or the like may be present as necessary when contacting the compound with a hydrocarbon solvent. When contacting with a hydrocarbon solvent, the hydrocarbon solvent is used at generally 1-30 volume ratio, preferably 3-20 volume ratio, particularly preferably 5-15 volume ratio, to the 2-naphthylacetic acid.

In the present invention, toluene is particularly preferable as the aforementioned hydrocarbon solvent because the removal of sulfur and the extraction of 2-naphthylacetic acid can be performed with a single solvent.

As described above, the 2-naphthylacetic acid obtained by contacting with a hydrocarbon solvent or the like in step 1 of the present invention has high quality with a sulfur content of 0.001 mol %-1 mol %, preferably 0.001 mol %-0.5 mol %, and a purity of not less than 98 mol %, preferably not less than 99 mol %.

(Isolation Method)

An organic solvent capable of dissolving 2-naphthylacetic acid (e.g., toluene, xylene, cyclohexane, etc.) is added to the reaction product obtained by the liberation reaction, the mixture is washed once or plural times with an appropriate washing solution such as water, an aqueous solution or the like, and 2-naphthylacetic acid may be isolated using a known method. For example, the mixture is stirred under acidic conditions (e.g., not more than pH3) with heating (e.g., 50° C.-90° C.), and washed, and the aqueous layer is separated, concentrated, and the like as necessary and cooled, whereby 2-naphthylacetic acid can be precipitated and recovered as a solid.

The 2-naphthylacetic acid obtained in step 1 is useful as a starting material for synthesis, or an intermediate for synthesis of various industrial products, pharmaceutical products and the like, and can be subjected to step 2 of the present invention.

<<Step 2>>

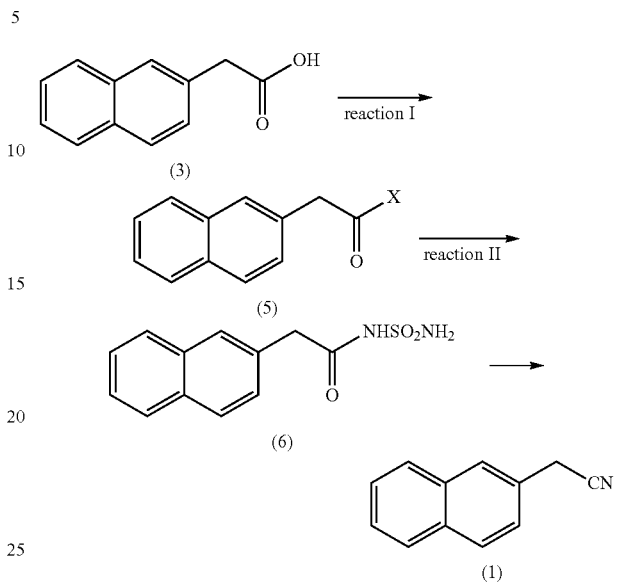

wherein X is a halogen atom.

In step 2, 2-naphthylacetonitrile represented by the formula (1) is obtained by the following two reactions I and II.
reaction I: A reaction in which 2-naphthylacetic acid represented by the formula (4) and a halogenating agent are mixed in a first organic solvent in the presence of a catalyst where necessary to give reaction starting material 1 containing a compound represented by the formula (5).
reaction II: A reaction in which reaction starting material 1 containing a compound represented by the formula (5) is mixed with reaction starting material 2 containing sulfamide and a second organic solvent to give 2-naphthylacetonitrile.

[Reaction I]

A reaction in which 2-naphthylacetic acid represented by the formula (3) and a halogenating agent are mixed in the first organic solvent in the presence of a catalyst where necessary to give reaction starting material 1 containing a compound represented by the formula (5).

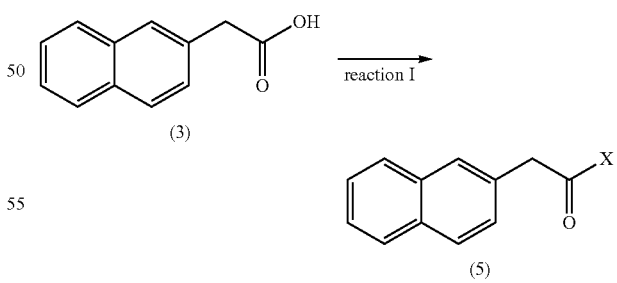

wherein X is a halogen atom.

<Starting Material>

(2-Naphthylacetic Acid)

As 2-naphthylacetic acid, one obtained in the aforementioned step 1 or a commercially available one can be used.

(Halogenating Agent)

The halogenating agent is not particularly limited as long as it can halogenate 2-naphthylacetic acid. As the halogenating agent, a chlorinating agent and a brominating agent are preferable, and a chlorinating agent is more preferable.

Examples of the chlorinating agent include thionyl chloride, oxalyl chloride, sulfuryl chloride, phosphoryl chloride, phosphorus trichloride, phosphorus pentachloride and the like.

Examples of the brominating agent include thionyl bromide, phosphorus tribromide and the like.

Among these, thionyl chloride, phosphoryl chloride, phosphorus pentachloride, thionyl bromide, and phosphorus tribromide are preferable, and thionyl chloride is particularly preferable, from the aspects of cost, broad utility, reactivity, and the like. As the halogenating agent, one kind may be used alone, or two or more kinds may be used in any combination and ratio.

The amount of the halogenating agent to be used is not particularly limited as long as it is an amount at which 2-naphthylacetic acid can be halogenated. For sufficient halogenation of the 2-naphthylacetic acid, generally, not less than 1 mol of the halogenating agent is preferably used per 1 mol of the 2-naphthylacetic acid.

While the upper limit is not particularly set on the amount to be used, not more than 3 mol per 1 mol of the 2-naphthylacetic acid is preferable from the aspects of cost, productivity and the like.

(Catalyst)

Reaction I can be performed in the presence of a catalyst where necessary. The catalyst is not particularly limited as long as it promotes the reaction. To enhance reactivity, reaction I is preferably performed in the presence of a catalyst.

Examples of the catalyst include tertiary amides such as N,N-dimethylformamide, N,N-dimethylacetamide, N-methylpyrrolidinone and the like. N,N-Dimethylformamide is particularly preferable since it is easily available and inexpensive.

The amount of the catalyst to be used is not particularly limited as long as it is an amount effective for functioning as a catalyst. The amount of the catalyst to be used is preferably 0.0001 mol-1 mol, more preferably 0.001 mol-0.1 mol, per 1 mol of the 2-naphthylacetic acid.

(First Organic Solvent)

The first organic solvent is not particularly limited as long as the reaction proceeds.

Examples of the first organic solvent include a hydrocarbon solvent, an amide solvent, a sulfoxide solvent, and a sulfone solvent. As these organic solvents, one kind may be used alone, or two or more kinds may be used in any combination and ratio.

As the hydrocarbon solvent, chain aliphatic hydrocarbons such as hexane, heptane and the like; cyclic aliphatic hydrocarbons such as cyclohexane, methylcyclohexane, cycloheptane and the like; aromatic hydrocarbons such as benzene, toluene, xylene, mesitylene, ethylbenzene, tert-butylbenzene and the like; or aromatic halogenated hydrocarbons such as trifluoromethylbenzene, nitrobenzene, chlorobenzene, chlorotoluene, bromobenzene and the like can be used.

As the amide solvent, aprotic amides such as N,N-dimethylformamide, N,N-dimethylacetamide, N-methylpyrrolidinone and the like can be used. Preferred is N,N-dimethylformamide.

As the sulfoxide solvent, aprotic sulfoxides such as dimethyl sulfoxide and the like can be used.

As the sulfone solvent, aprotic sulfones such as ethyl methyl sulfone, ethyl isopropyl sulfone, 3-methylsulfolane, sulfolane and the like can be used. Preferred is sulfolane.

In view of the superiority in operability, productivity and the like, and cost and the like, the first organic solvent is preferably a hydrocarbon solvent, an amide solvent, or a sulfone solvent, more preferably a hydrocarbon solvent or an amide solvent, among which toluene, xylene, chlorobenzene and N,N-dimethylformamide are more preferred, and toluene is particularly preferred.

Furthermore, in view of the superiority in reactivity, operability, productivity and the like, and cost and the like, a mixture of a hydrocarbon solvent and an amide solvent is also preferably used as the first organic solvent, and a mixture of toluene and N,N-dimethylformamide is particularly preferred. The mixing ratio (volume ratio) of the hydrocarbon solvent and the amide solvent can be appropriately selected from the range of 1:99-99:1.

The amount of the first organic solvent to be used is generally not less than 1 L, preferably not less than 2 L, further preferably not less than 3 L, per 1 kg of the 2-naphthylacetic acid, from the aspects of operability and the like, and the upper limit is generally not more than 50 L, preferably not more than 30 L, more preferably not more than 20 L, further preferably not more than 10 L, particularly preferably not more than 4.5 L, most preferably not more than 4 L, per 1 kg of the 2-naphthylacetic acid, from the aspects of the operability, productivity, cost and the like.

(Inorganic Additive)

In the reaction I, where necessary, an inorganic additive (e.g., diatomaceous earth, silicic anhydride, silicon dioxide, sodium sulfate, magnesium sulfate, sodium chloride, magnesium chloride, calcium carbonate, magnesium carbonate, etc.) may be added. Using an inorganic additive, the reaction can proceed smoothly.

<Reaction Conditions>

(Reaction Temperature)

The reaction temperature is generally 15° C.-70° C., preferably 20° C.-65° C., particularly preferably 30° C.-60° C. When the reaction temperature is too low, the progress of the reaction may be delayed and the productivity may decrease, and when it is too high, by-products may be produced and the quality may decrease.

(Reaction Time)

The reaction time is generally 0.5 hr-30 hr, preferably 1 hr-15 hr, particularly preferably 2 hr-10 hr.

(Reaction Pressure)

While the reaction pressure is generally normal pressure, the reaction may also be performed under pressurization.

<Post-Treatment>

When the reaction mixture obtained in reaction I which contains a compound represented by the formula (5) is used for reaction II, the reaction mixture may be used as it is, or a concentrated liquid obtained by concentrating the reaction mixture may be used, or an organic layer obtained by neutralizing the reaction mixture by mixing water or an alkaline aqueous solution and separating the layer may be used. Alternatively, a poor solvent may be added to the organic layer for crystallization, and crystals obtained by a treatment such as filtration and the like may also be used. Furthermore, the product obtained in reaction I may be purified by a known purification means such as column chromatography and the like. In the production method of the present invention, the reaction mixture or the concentrated liquid is preferably used as it is for reaction II from the aspects of cost and productivity.

[Reaction II]

A reaction in which a compound represented by the formula (5), sulfamide and the second organic solvent are mixed to give 2-naphthylacetonitrile represented by the formula (1).

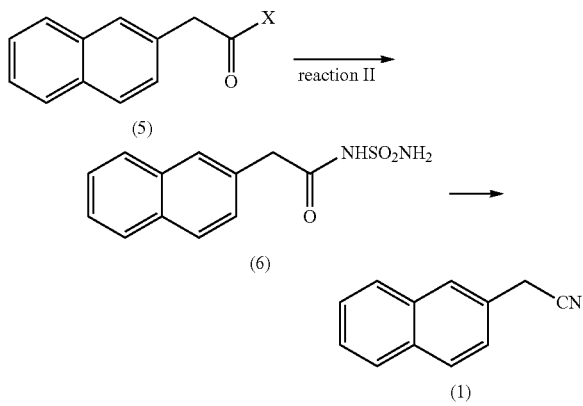

wherein X is a halogen atom.

This reaction II can suppress production of the naphthalene compounds (by-products) explained in the aforementioned "high purity 2-naphthylacetonitrile of the present invention".

<Starting Material>
(Compound Represented by the Formula (5))

As the compound represented by the formula (5), one obtained in reaction I can be used. It is preferable to use a concentrated liquid obtained by concentrating the reaction mixture obtained in reaction I from the aspect of producibility.

(Sulfamide)

As sulfamide, a commercially available product can be used.

The amount of the sulfamide to be used is generally preferably not less than 1 mol per 1 mol of 2-naphthylacetic acid. The amount of the sulfamide to be used is generally 1 mol-5 mol, preferably 1.02 mol-3 mol, more preferably 1.03 mol-2 mol, particularly preferably 1.05 mol-1.5 mol, per 1 mol of 2-naphthylacetic acid.

(Second Organic Solvent)

As the second organic solvent, the same organic solvent as the aforementioned first organic solvent can be used, and a sulfone solvent is preferable. From the aspects of reactivity, productivity and the like, sulfolane is preferred.

Furthermore, as the second organic solvent, a mixture of a hydrocarbon solvent and a sulfone solvent is also preferably used, and a mixture of toluene and sulfolane is particularly preferable. The mixing ratio (volume ratio) of the hydrocarbon solvent and the sulfone solvent can be appropriately selected within the range of 1:99-99:1.

The amount of the second organic solvent to be used is generally not less than 1 L, preferably not less than 2 L, further preferably not less than 3 L, per 1 kg of the 2-naphthylacetic acid, from the aspects of operability and the like, and the upper limit is generally not more than 50 L, preferably not more than 30 L, more preferably not more than 20 L, further preferably not more than 4.5 L, particularly preferably not more than 4 L, per 1 kg of the 2-naphthylacetic acid, from the aspects of the operability, productivity, cost and the like.

(Inorganic Additive)

In the reaction II, where necessary, an inorganic additive (e.g., diatomaceous earth, silicic anhydride, silicon dioxide, sodium sulfate, magnesium sulfate, sodium chloride, magnesium chloride, calcium carbonate, magnesium carbonate, etc.) may be added. Using an inorganic additive, the reaction can proceed smoothly.

<Reaction Conditions>
(Reaction Temperature)

The reaction temperature may vary depending on the organic solvent, catalyst and the like to be used. The lower limit is generally not less than 80° C., preferably not less than 85° C., particularly preferably not less than 90° C., from the aspects of quality, reactivity and the like. The upper limit is generally not more than 180° C., preferably not more than 150° C., further preferably not more than 120° C., particularly preferably not more than 110° C., from the aspects of quality, reactivity, cost and the like.

When the reaction temperature is too low, the progress of the reaction may be delayed and the productivity may decrease, and when it is too high, by-products may be produced and the yield and quality of 2-naphthylacetonitrile of a target compound may decrease.

In this embodiment, the reaction starting material 1 and the reaction starting material 2 may be mixed and the mixture may be heated and reacted at 80° C.-180° C., or the reaction starting material 1 at 80° C.-180° C. and the reaction starting material 2 at 80° C.-180° C. may be mixed and reacted. The reaction starting material 2 may be added to the reaction starting material 1 and mixed, or the reaction starting material 1 may be added to the reaction starting material 2 and mixed.

(Reaction Time)

The time of reaction of the reaction starting material 1 and the reaction starting material 2 may vary depending on the halogenating agent, organic solvent, catalyst and the like to be used, and can be appropriately determined according to the progress of the reaction. It is generally 0.5 hr-48 hr, preferably 1 hr-24 hr, particularly preferably 2 hr-12 hr. When the reaction proceeds from the start of mixing, the reaction time means the time from the start of mixing of the reaction starting material 1 and the reaction starting material 2 to the post-treatment.

(Reaction Pressure)

The reaction is generally performed under normal pressure, but may also be performed under pressurization.

(Reaction Method)

While the production method of the present invention may be of a batch type or a continuous type, it is generally of a batch type.

(Order of Supply)

The order of supply of the reaction starting material 1 and the reaction starting material 2 can be appropriately selected. For example, the reaction starting material 1 may be placed in a reactor, and the reaction starting material 2 may be supplied and mixed, or the reaction starting material 2 may be placed in a reactor, and the reaction starting material 1 may be supplied and mixed, or the reaction starting materials 1 and 2 may be supplied at the same time into a reactor and mixed.

By making the temperature of the mixture of the reaction starting material 1 and the reaction starting material 2 relatively low with respect to the reaction temperature, the production of by-products due to overreaction is suppressed, and higher purity 2-naphthylacetonitrile can be produced efficiently at a low cost even in mass synthesis on an industrial scale.

(Supply Method)

The supply method includes, for example, a method of adding the entire amount of the reaction starting material 1 to the reaction starting material 2 at once, a method of dividing the reaction starting material 1 into two or more and adding the two or more portions at time intervals, a method of adding a given amount intermittently or continuously by dropwise addition and the like, and the like.

In the present invention, a method of dividing into two or more and adding them, and a method of adding a given amount intermittently or continuously by dropwise addition and the like are preferable to suppress formation of by-products. In this case, the reaction starting material 1 is added to the reaction starting material 2 such that the amount of the acid halide compound represented by the aforementioned formula (5) contained in the reaction starting material 1 (addition amount per min) is not less than 0.0027 mol/min, preferably not less than 0.0035 mol/min, particularly preferably not less than 0.0069 mol/min, per 1 mol of sulfamide contained in the reaction starting material 2. By setting the addition amount to not less than 0.0027 mol/min, the amount of the acid halide compound represented by the aforementioned formula (5) in the reaction mixture of the reaction starting material 1 and the reaction starting material 2 can be set to an appropriate range, and it is considered that formation of by-products can be suppressed. Particularly, it is considered that the production of a naphthalene compound represented by the formula (c) can be suppressed.

In this case, the time for adding the reaction starting material 1 to the reaction starting material 2 can be appropriately selected according to the addition amount of the above-mentioned reaction starting material 1. It is generally not less than 5 min, preferably not less than 10 min.

When the addition amount is less than 0.0027 mol/min, the production of by-products may increase. Furthermore, when the addition time is too short, a large amount of gas produced as a by-product due to the reaction between the reaction starting material 1 and the reaction starting material 2 may be rapidly generated.

(Temperature of Mixture)

The temperature of the mixture obtained by mixing the reaction starting material 1 and the reaction starting material 2 may vary depending on the organic solvent, catalyst and the like to be used. The lower limit is generally not less than 10° C., preferably not less than 15° C., particularly preferably not less than 20° C., from the aspects of quality, reactivity and the like. The upper limit is generally not more than 100° C., preferably not more than 95° C., particularly preferably not more than 90° C., from the aspects of quality, reactivity, cost and the like.

When the temperature of the mixture obtained by mixing the reaction starting material 1 and the reaction starting material 2 is less than 15° C., the mixing may be insufficient and the reaction efficiency may decrease. When it is higher than 90° C., the production of by-products may increase. Particularly, when the temperature of the mixture is high, a compound represented by the formula (5) reacts with the reaction product, and impurities such as the compound represented by the formula (c) and the like are easily produced. Thus, the yield and quality of 2-naphthylacetonitrile represented by the formula (1) may decrease.

(c)

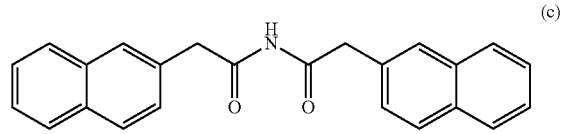 [SMILES: O=C(Cc1ccc2ccccc2c1)NC(=O)Cc1ccc2ccccc2c1]

<Post-Treatment>

The reaction mixture containing 2-naphthylacetonitrile obtained in the aforementioned step 2 may be subjected to treatments such as neutralization, partitioning, filtration and the like, or the desired 2-naphthylacetonitrile may be isolated by isolation means such as concentration, crystallization with an organic solvent such as toluene, heptane or the like, and the like. In addition, the desired nitrile compound can be precipitated as crystals by adding a poor solvent such as water and the like to a reaction mixture containing the 2-naphthylacetonitrile.

For example, the obtained reaction mixture is cooled, an organic solvent such as toluene and the like is added, the organic layer is washed with water and a base, the organic layer obtained by washing is concentrated, an organic solvent such as methanol and the like is added to the concentrated residue for solvent substitution, the mixture is cooled, the precipitated 2-naphthylacetonitrile is collected by filtration, and the obtained wet crystals are dried, whereby 2-naphthylacetonitrile can be obtained as a solid.

The 2-naphthylacetonitrile obtained in the present invention has a high quality of purity (HPLC) of preferably not less than 98 area %, particularly preferably not less than 99 area %. It may be further purified by a known purification means such as recrystallization, column chromatography, activated carbon treatment and the like.

In addition, each compound in the present invention may form a solvate such as hydrate, organic solvent solvate, and the like, and the form thereof is not particularly limited as long as the reaction is not inhibited.

In the production method of the present invention, the following steps are particularly preferable as step 1 and step 2.

step 1: a step of reacting 2'-acetonaphthone, sulfur and morpholine, followed by hydrolysis to give 2-naphthylacetic acid

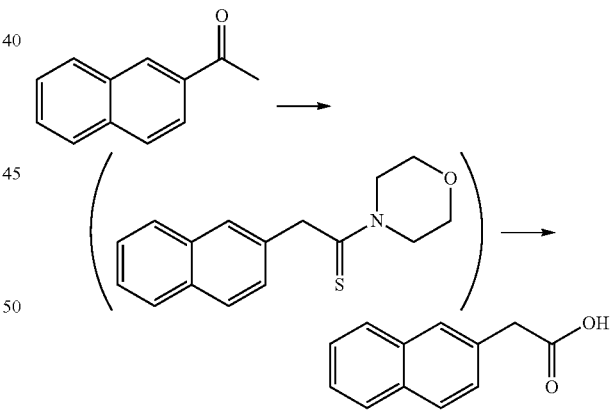

step 2: a step of mixing a reaction starting material 1 which is a mixture of 2-naphthylacetic acid, thionyl chloride, toluene and, where necessary, a catalyst with a reaction starting material 2 which is a mixture of sulfamide and sulfolane at 15° C.-90° C., raising the temperature and reacting the mixture at 80° C.-180° C. to give 2-naphthylacetonitrile, or a step of adding the above-mentioned reaction starting material 1 to the above-mentioned reaction starting material 2, and reacting the mixture at 80° C.-180° C. to give 2-naphthylacetonitrile, wherein the reaction starting material 1 is added to the reaction starting material 2 such that the amount of an acid chloride contained in the reaction starting material 1 is not less than 0.0027 mol/min per 1 mol of sulfamide contained in the reaction starting material 2.

This step 2 can suppress production of the naphthalene compounds (by-products), particularly the naphthalene compound represented by the formula (c), explained in the aforementioned "high purity 2-naphthylacetonitrile of the present invention".

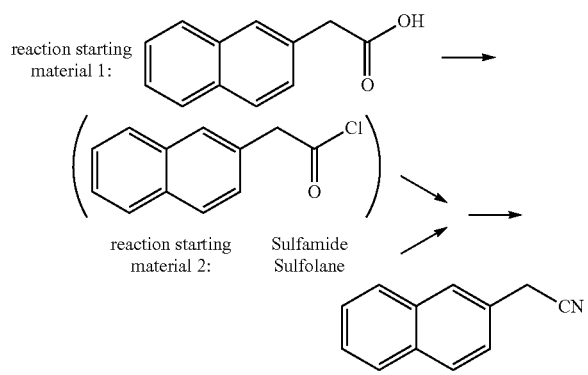

EXAMPLES

The present invention is described in more detail with reference to Examples; however, the present invention is not limited by these examples.

In the following Examples and Comparative Examples, commercially available 2'-acetonaphthone was used. The purity of the obtained compound was measured by HPLC under the following analysis conditions.

(HPLC Analysis Conditions)

analysis instrument: HPLC (1200 series) manufactured by Agilent column: Zorbax Eclipse Plus Phenyl-Hexyl, 5 μm, 250 mm×4.6 mm mobile phase A: 0.1 volume % trifluoroacetic acid aqueous solution mobile phase B: acetonitrile gradient: 0 min (B:30%)—15 min (B:60%)—20 min (B:95%)—30 min (B:95%)

flow rate: 1.0 mL/min injection volume: 5 μL detection wavelength: 280 nm column temperature: 40° C.

Example 1

(1) Synthesis of 2-naphthylacetic acid

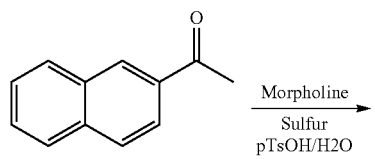

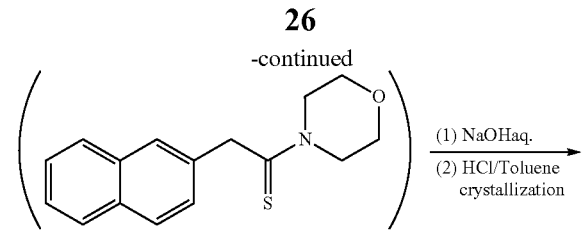

In a nitrogen-substituted reactor were placed 2'-acetonaphthone (24 kg), sulfur (5.65 kg) (1.25 mole ratio to 2'-acetonaphthone), p-toluenesulfonic acid monohydrate (2.68 kg) (0.1 mole ratio to 2'-acetonaphthone) and morpholine 36.9 kg (3 mole ratio to 2'-acetonaphthone), and the mixture was stirred and reacted at 115° C.-120° C. for 3 hr. Here, the production of the thioamide compound was confirmed by HPLC.

The reaction mixture was cooled to 70° C.-80° C., sodium hydroxide aqueous solution at concentration 20 wt % (mixture of sodium hydroxide (16.9 kg) and water (67.7 kg), sodium hydroxide at 5 mole ratio to 2'-acetonaphthone) was added, water (43.2 kg) was further added, and the mixture was heated and reacted at 90° C.-105° C. for 4 hr (hydrolysis).

The obtained reaction mixture was cooled to 65° C.-75° C., water (24 kg) and toluene (83.2 kg) were added, the mixture was stirred at 65° C.-75° C. and allowed to stand, and the obtained upper layer was discarded (removal of unreacted sulfur). The remaining lower layer (206.35 kg) was added to a mixture of toluene (208.05 kg) and hydrochloric acid (80.8 kg) at a concentration of 35 wt %. The reactor that contained the lower layer was washed with water (2.4 kg). The liquid obtained after washing was also added to the aforementioned mixture. A mixture containing the thus-obtained reaction mixture was stirred at 65° C.-75° C., and allowed to stand (extraction of 2-naphthylacetic acid), and the obtained lower layer was discarded. To the remaining upper layer was added water (121.0 kg), and the mixture was stirred at 65° C.-75° C. and allowed to stand, and the lower layer was discarded. To the remaining upper layer was added water (121 kg), and the mixture was stirred at 65° C.-75° C. and allowed to stand, and the lower layer was discarded.

The remaining upper layer was concentrated and cooled to not more than 10° C. The precipitated crystals of 2-naphthylacetic acid were collected by centrifugation and washed with toluene (20.8 kg) to give wet crystals. The obtained wet crystals were dried under reduced pressure under temperature condition at 60° C. to give 2-naphthylacetic acid (19.70 kg).

$^1$H-NMR (400 MHz, CDCl$_3$) δ 3.80 (2H, s), 7.40 (1H, dd, J=8.4, 3.0 Hz), 7.43-7.49 (2H, m), 7.73 (1H, s), 7.78-7.82 (3H, m)

(2) Synthesis of 2-naphthylacetonitrile

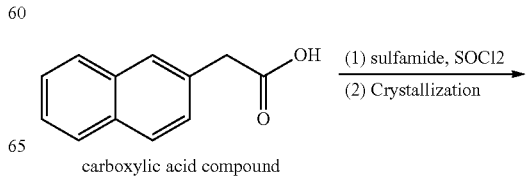

carboxylic acid compound

-continued

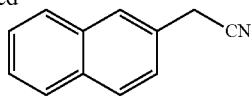

In a nitrogen-substituted reactor were added 2-naphthylacetic acid (18.7 kg) obtained in the above-mentioned (1), toluene (40.55 kg), and N,N-dimethylformamide (73.08 g). The instrument used for the above-mentioned addition was washed with toluene (16.2 kg) and the liquid obtained after washing was also added to the reactor. To the obtained solution was added thionyl chloride (12.5 kg) (1.05 mole ratio to 2-naphthylacetic acid), and the mixture was reacted at 35° C.-45° C. for 5 hr. After cooling to 20° C.-30° C., the mixture was filtered. The obtained filtrate was mixed with a washing obtained by washing the filtration residue with toluene (8.15 kg), sulfolane (23.6 kg) (1 volume ratio to 2-naphthylacetic acid) was added, and the mixture was concentrated under reduced pressure to prepare an acid chloride solution.

In another nitrogen-substituted reactor were placed sulfamide (11.6 kg) (1.2 mole ratio to 2-naphthylacetic acid), sulfolane (58.9 kg) (2.5 volume ratio to 2-naphthylacetic acid) and an inorganic additive (18.7 kg), and the mixture was stirred and heated to 95° C.-105° C. to prepare a sulfamide solution.

The acid chloride solution was added dropwise to the sulfamide solution over 2 hr at 95° C.-105° C. The reactor that contained the acid chloride solution was washed with toluene (1.62 kg). The liquid obtained after washing was also added to the reactor, and the mixture was reacted at 95° C.-105° C. for 7 hr.

The obtained reaction mixture was cooled to 25° C., toluene (65 kg) and water (74.8 kg) were added, the mixture was stirred at 20° C.-30° C. and allowed to stand, and the lower layer was discarded. To the remaining upper layer were added water (35.5 kg) and potassium carbonate (5.61 kg). The instrument used for the above-mentioned reaction was washed with water (15 kg) and the liquid obtained after washing was also added to a mixture containing the above-mentioned upper layer. The obtained mixture was stirred at 20° C.-30° C. and allowed to stand, and the lower layer was discarded. To the remaining upper layer was added water (37.4 kg), the mixture was stirred at 20° C.-30° C. and allowed to stand, and the lower layer was discarded. The remaining upper layer was concentrated, methanol (104 kg) was added, and the mixture was further concentrated. To the obtained concentrated liquid was added methanol (44.4 kg), and the mixture was concentrated. To the obtained concentrated liquid were added activated carbon (0.374 kg) and methanol (45.1 kg) at 35° C., and the mixture was stirred and filtered. The filtration residue was washed with methanol (14.95 kg), and the filtrate and the liquid after washing were mixed.

The obtained mixed solution was maintained at 30° C.-40° C. for about 90 min and cooled, water (74.8 kg) (4 volume ratio to 2-naphthylacetic acid) was added at a temperature near 10° C., and the mixture was stirred for 4 hr. The precipitated crystals were collected by centrifugation, and the collected wet crystals were washed with a methanol aqueous solution (mixed solution of methanol (14.8 kg) and water (18.7 kg)). The obtained wet crystals were dried under reduced pressure under temperature condition at 60° C. to give 2-naphthylacetonitrile as crystals (15.2 kg, purity 99.50 area %).

$^1$H-NMR (400 MHz, CDCl$_3$) δ 3.92 (2H, s), 7.37-7.40 (1H, m), 7.49-7.54 (2H, m), 7.83-7.85 (4H, m)

The HPLC analysis results of the obtained 2-naphthylacetonitrile are shown in Table 3 and FIG. 1. In Table 3, RRT is a relative retention time when the retention time of 2-naphthylacetonitrile is 1.00.

TABLE 3

| | compound | RRT | content (area %) |
|---|---|---|---|
| | 2-naphthylacetonitrile | 1.00 | 99.50 |
| impurities | compound of the formula (a) | 1.09 | 0.20 |
| | compound of the formula (b) | 1.23 | 0.06 |
| | compound of the formula (c) | 1.39 | 0.15 |
| | compound of the formula (d) | 1.63 | 0.02 |
| | other impurity | — | 0.07 |

From the HPLC analysis results, the compounds of the formulas (e)-(j) were not detected in the obtained 2-naphthylacetonitrile.

The $^1$H-NMR measurement results of the compounds of the formulas (a)-(d) are as follows.

Compound of Formula (a)

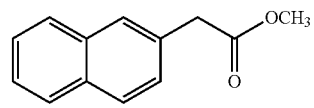 [SMILES: COC(=O)Cc1ccc2ccccc2c1]

$^1$H-NMR (400 MHz, CDCl$_3$) δ=3.71 (s, 3H), 3.79 (s, 2H), 7.40-7.47 (m, 3H), 7.73 (s, 1H), 7.79-7.83 (m, 3H)

Compound of Formula (b)

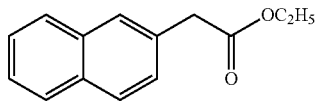 [SMILES: CCOC(=O)Cc1ccc2ccccc2c1]

LC/MS 215 (m/z, Pos)

$^1$H-NMR (400 MHz, CDCl$_3$) δ=1.26 (t, J=7.2 Hz, 3H), 3.78 (s, 2H), 4.17 (q, J=7.2 Hz, 2H), 7.41-7.49 (m, 3H), 7.74 (s, 1H), 7.79-7.82 (m, 3H)

Compound of Formula (c)

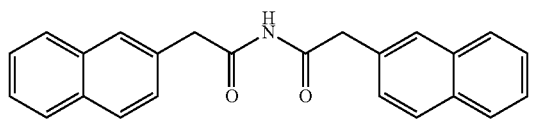 [SMILES: O=C(Cc1ccc2ccccc2c1)NC(=O)Cc1ccc2ccccc2c1]

LC/MS 354 (m/z, Pos)

$^1$H-NMR (400 MHz, dmso-d$_6$) δ=4.03 (s, 4H), 7.41 (dd, J=8.4, 1.6 Hz, 2H), 7.48-7.50 (m, 4H), 7.75 (s, 2H), 7.82-7.90 (m, 6H), 11.12 (s, 1H)

Compound of Formula (d)

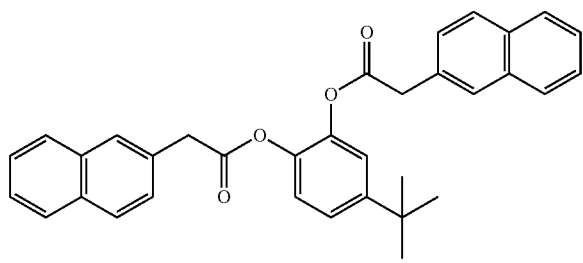 [SMILES: CC(C)(C)c1ccc(OC(=O)Cc2ccc3ccccc3c2)c(OC(=O)Cc2ccc3ccccc3c2)c1]

LC/MS 503 (m/z, Pos)
¹H-NMR (400 MHz, CDCl₃) δ=1.27 (s, 9H), 3.54 (s, 2H), 3.59 (s, 2H), 7.04 (d, J=8.8 Hz, 1H), 7.11 (d, J=2.0 Hz, 1H), 7.21 (dd, J=8.4, 2.4 Hz, 1H), 7.29-7.34 (m, 2H), 7.42-7.49 (m, 4H), 7.59 (s, 1H), 7.63 (s, 1H), 7.76-7.79 (m, 6H)

Example 2

In a nitrogen-substituted reactor were added 2-naphthylacetic acid (75.02 g) synthesized according to the method of Example 1(1), toluene (263 mL) (3.5 volume ratio to 2-naphthylacetic acid), and N,N-dimethylformamide (0.29 g) (0.01 mole ratio to 2-naphthylacetic acid), the mixture was heated, and thionyl chloride (50.3 g) (1.05 mole ratio to 2-naphthylacetic acid) was added at 35° C.-45° C. After reaction for 3 hr, the reaction mixture was concentrated and reaction starting material 1 containing 2-naphthylacetyl chloride was prepared.

In another nitrogen-substituted reactor were added sulfamide (46.49 g) (1.2 mole ratio to 2-naphthylacetic acid), an inorganic additive (74.99 g) (1 weight ratio to 2-naphthylacetic acid), and sulfolane (263 mL) (3.5 volume ratio to 2-naphthylacetic acid), and the mixture was heated (preparation of reaction starting material 2). The reaction starting material 1 containing 2-naphthylacetyl chloride was added dropwise to the reaction starting material 2 at 95° C.-105° C. over 18 min. The instrument used for preparing the reaction starting material 1 was washed with toluene (7.5 mL) (0.1 volume ratio to 2-naphthylacetic acid), the obtained solution was further added to the reaction starting material 2, and the mixture was reacted at 95° C.-105° C. for 4 hr. The reaction mixture was analyzed by HPLC, and the disappearance of the starting materials was confirmed. Then, the mixture was cooled to 20° C.-30° C., water (300 mL) (4 volume ratio to 2-naphthylacetic acid) and toluene (300 mL) (4 volume ratio to 2-naphthylacetic acid) were added, the mixture was stirred, and the aqueous layer was discarded. The remaining organic layer was washed with 10 wt % potassium carbonate aqueous solution (225.08 g) (3 weight ratio to 2-naphthylacetic acid) and water (150 mL) (2 volume ratio to 2-naphthylacetic acid).

The obtained organic layer was concentrated, methanol (525 mL) (7 volume ratio to 2-naphthylacetic acid) was added to the concentrated residue, and the mixture was concentrated again. Furthermore, methanol was added to the obtained concentrated residue to adjust the liquid amount to 525 mL. Activated carbon (1.52 g) (0.02 weight ratio to 2-naphthylacetic acid) was added, and the mixture was stirred at 50° C.-60° C. and filtered. The obtained filtration residue was washed with methanol (75 mL) (1 volume ratio to 2-naphthylacetic acid).

The obtained filtrate and washing solution were cooled to 5° C.-15° C., water (300 mL) (4 volume ratio to 2-naphthylacetic acid) was added, and the mixture was stirred. The precipitated 2-naphthylacetonitrile was collected by filtration, and the obtained wet crystals were dried to obtain 2-naphthylacetonitrile (60.38 g) (purity 99.85 area %) as a solid.

The HPLC analysis results of the reaction mixture after reaction for 4 hr and the obtained 2-naphthylacetonitrile are shown in Table 4.

TABLE 4

| compound | | RRT | reaction mixture after reaction for 4 hr (area %) | crystal (area %) |
|---|---|---|---|---|
| 2-naphthylacetonitrile | | 1.00 | 96.50 | 99.85 |
| impurities | compound of the formula (a) | 1.08 | not detected | 0.04 |
| | compound of the formula (b) | 1.22 | 0.87 | 0.05 |
| | compound of the formula (c) | 1.35 | 0.15 | 0.06 |
| | other impurity | — | 2.48 | not detected |

From the HPLC analysis results, the compounds of the formulas (d)-(j) were not detected in the obtained crystal of 2-naphthylacetonitrile.

Example 3

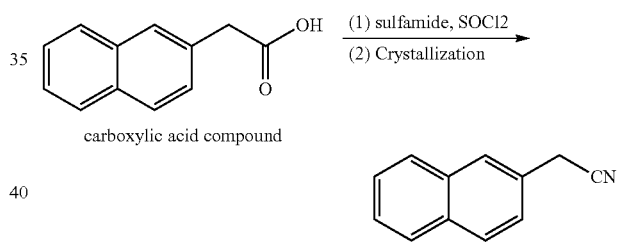

carboxylic acid compound

In a nitrogen-substituted reactor were added 2-naphthylacetic acid (25 g) synthesized according to the method of Example 1(1), toluene (75.88 g) (3.5 volume ratio to 2-naphthylacetic acid), and N,N-dimethylformamide (0.0982 g) (0.01 mole ratio to 2-naphthylacetic acid). To the obtained solution was added dropwise thionyl chloride (16.77 g) (1.05 mole ratio to 2-naphthylacetic acid), and the mixture was reacted at 43° C.-45° C. for 3 hr. Toluene (10.88 g) (0.5 volume ratio to 2-naphthylacetic acid) and sulfolane (31.53 g) (1 volume ratio to 2-naphthylacetic acid) were added, and the mixture was concentrated under reduced pressure to prepare reaction starting material 1 containing 2-naphthylacetyl chloride.

In another nitrogen-substituted reactor were added sulfamide (15.5 g) (1.2 mole ratio to 2-naphthylacetic acid), sulfolane (78.78 g) (2.5 volume ratio to 2-naphthylacetic acid), and an inorganic additive (25.01 g), and the mixture was stirred and heated to 75° C.-85° C. (preparation of reaction starting material 2). The reaction starting material 2 was not a solution but a slurry.

The reaction starting material 1 containing 2-naphthylacetyl chloride was added dropwise to the reaction starting material 2 at 75° C.-85° over 10 hr, and the mixture was heated to 100° C. over 2 hr and reacted for 5 hr.

The obtained reaction mixture was cooled to 55° C.-65° C., toluene (86.7 g) (4 volume ratio to 2-naphthylacetic acid) and water (100.05 g) (4 volume ratio to 2-naphthylacetic acid) were added. The mixture was stirred and allowed to stand, and the lower layer was discarded. To the remaining upper layer was added 5 wt % aqueous sodium hydrogen carbonate solution (75.01 g) (3 weight ratio to 2-naphthylacetic acid). The mixture was stirred at 55° C.-65° C. and allowed to stand, and the lower layer was discarded. To the remaining upper layer was added water (50.01 g) (2 weight ratio to 2-naphthylacetic acid), the mixture was stirred at 55° C.-65° C. and allowed to stand, and the lower layer was discarded. The remaining upper layer was concentrated, methanol (138.44 g) (7 volume ratio to 2-naphthylacetic acid) was added to the concentrated residue, and the mixture was further concentrated. To the obtained concentrated residue was added methanol (59.34 g) (3 volume ratio to 2-naphthylacetic acid), and the mixture was concentrated. To the concentrated residue were added methanol (39.55 g) (2 volume ratio to 2-naphthylacetic acid) and activated carbon (0.5 g) (0.02 weight ratio to 2-naphthylacetic acid), and the mixture was filtered. The obtained filtrate was mixed with a washing obtained by washing the filtration residue with methanol (19.78 g) (1 volume ratio to 2-naphthylacetic acid) to give a 2-naphthylacetonitrile solution.

The obtained 2-naphthylacetonitrile solution was heated to 40° C.-50° C., water (0.1259 g) (0.005 volume ratio to 2-naphthylacetic acid) and potassium carbonate (0.0248 g) (0.001 weight ratio to 2-naphthylacetic acid) were added, and the mixture was stirred for 1 hr. Water (100 g) (4 volume ratio to 2-naphthylacetic acid) was added dropwise over 1 hr. Thereafter, the mixture was cooled and stirred at a temperature near 10° C. for 1 hr. The precipitated crystals were collected by filtration, and the collected wet crystals were washed twice with a methanol aqueous solution (mixed solution of methanol (27.71 g) and water (15.03 g)). The obtained wet crystals were dried under reduced pressure under temperature condition at 60° C. to give 2-naphthylacetonitrile as crystals (19.09 g, yield 85%, purity 99.87 area %).

Figure 2:
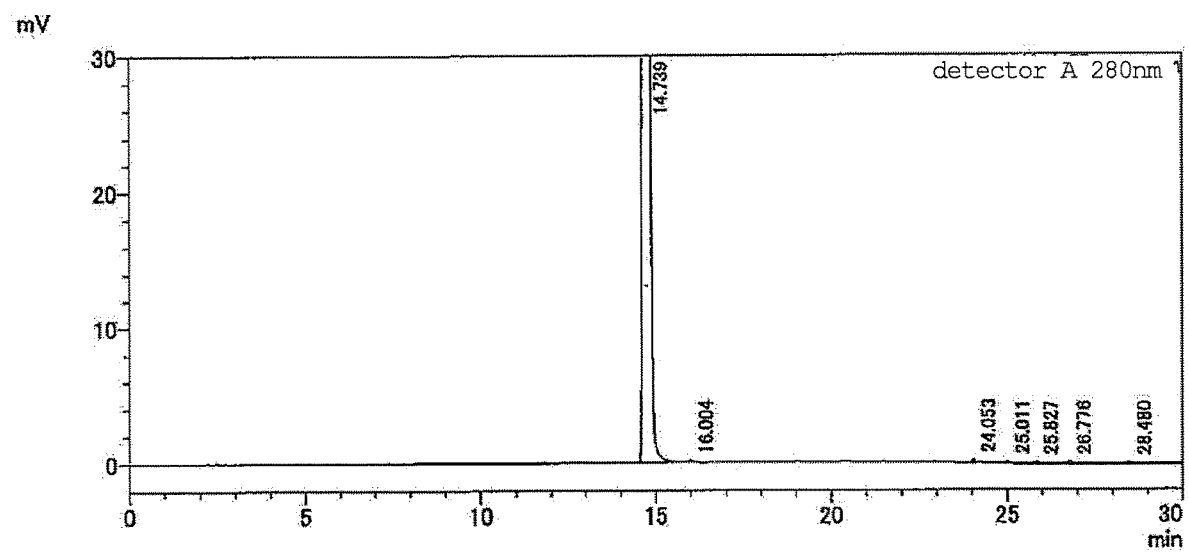
FIG. 2 shows the HPLC analysis results of 2-naphthylacetonitrile obtained in Example 3.

The HPLC analysis results of the obtained 2-naphthylacetonitrile are shown in Table 5 and FIG. 2.

TABLE 5

| | compound | RRT | content (area %) |
|---|---|---|---|
| | 2-naphthylacetonitrile | 1.00 | 99.87 |
| impurities | compound of the formula (a) | 1.08 | 0.02 |
| | compound of the formula (c) | 1.39 | not detected |
| | compound of the formula (d) | 1.63 | 0.02 |

From the HPLC analysis results, the compounds of the formulas (b) and (e)-(j) were not detected in the obtained crystal of 2-naphthylacetonitrile. According to this Example, 2-naphthylacetonitrile having a lower content of impurities, for example, the compounds of the formula (a) and the formula (c), than in Examples 1 and 2 was obtained. In particular, the 2-naphthylacetonitrile obtained in this Example does not contain the compound of the formula (c) and is useful as a starting material or intermediate for the synthesis of pharmaceutical products.

As described above, it is clear that high purity 2-naphthylacetonitrile with a small content of impurities can be obtained by mixing reaction starting material 1 containing 2-naphthylacetyl chloride and reaction starting material 2 containing sulfamide at a comparatively low temperature, and heating and reacting the mixture.

Example 4

In a nitrogen-substituted reactor were added 2-naphthylacetic acid (10.03 g) synthesized according to the method of Example 1(1), toluene (35 mL) (3.5 volume ratio to 2-naphthylacetic acid), and N,N-dimethylformamide (42 µL) (0.01 mole ratio to 2-naphthylacetic acid), the mixture was heated, and thionyl chloride (6.72 g) (1.05 mole ratio to 2-naphthylacetic acid) was added at 35° C.-45° C. After reacting for 2 hr, the mixture was cooled and filtered at room temperature, and the filtration residue was washed with toluene (5 mL). To the obtained filtrate and washing solution was added sulfolane (10 mL) (1 volume ratio to 2-naphthylacetic acid), the mixture was concentrated, and reaction starting material 1 containing 2-naphthylacetyl chloride was prepared.

In another nitrogen-substituted reactor were added sulfamide (6.19 g) (1.2 mole ratio to 2-naphthylacetic acid), an inorganic additive (10.01 g) (1.0 weight ratio to 2-naphthylacetic acid), and sulfolane (25 mL) (2.5 volume ratio to 2-naphthylacetic acid), and the mixture was heated (preparation of reaction starting material 2). The reaction starting material 1 containing 2-naphthylacetyl chloride was added dropwise to the reaction starting material 2 at 95° C.-105° over 1 hr. The instrument used for preparing the reaction starting material 1 was washed with toluene (1 mL) (0.1 volume ratio to 2-naphthylacetic acid), the obtained solution was further added, and the mixture was reacted at 95° C.-105° C. for 4 hr. The reaction mixture was analyzed by HPLC. As a result, 2-naphthylacetonitrile (96.27 area %) and the compound of the formula (c) (0.39 area %) were contained.

The reaction mixture was cooled to 25° C., water (40 mL) (4 volume ratio to 2-naphthylacetic acid) and toluene (40 mL) (4 volume ratio to 2-naphthylacetic acid) were added, the mixture was stirred, and the lower layer was discarded. The remaining organic layer was washed with 10 wt % potassium carbonate aqueous solution (30.32 g) (3 weight ratio to 2-naphthylacetic acid) and water (20 mL) (2 volume ratio to 2-naphthylacetic acid).

The obtained organic layer was concentrated, methanol (70 mL) (7 volume ratio to 2-naphthylacetic acid) was added to the concentrated residue, and the mixture was concentrated again. Furthermore, methanol was added to the obtained concentrated residue to adjust the liquid amount to 70 mL. Activated carbon (0.2 g) (0.02 weight ratio to 2-naphthylacetic acid) was added, and the mixture was stirred at 40° C.-50° C. and filtered. The obtained filtration residue was washed with methanol (10 mL) (1 volume ratio to 2-naphthylacetic acid).

The obtained filtrate and washing solution were cooled to 5° C.-15° C., water (40 mL) (4 volume ratio to 2-naphthylacetic acid) was added, and the mixture was stirred. The precipitated 2-naphthylacetonitrile was collected by filtration, and the obtained wet crystals were dried to obtain 2-naphthylacetonitrile (8.11 g) (purity 99.30 area %) as a solid.

The HPLC analysis results of the reaction mixture after reaction for 4 hr and the obtained 2-naphthylacetonitrile are shown in Table 6.

TABLE 6

| compound | | RRT | reaction mixture after reaction for 4 hr (area %) | crystal (area %) |
|---|---|---|---|---|
| 2-naphthylacetonitrile | | 1.00 | 96.27 | 99.30 |
| impurities | compound of the formula (a) | 1.08 | not detected | 0.06 |
| | compound of the formula (b) | 1.22 | 0.62 | not detected |
| | compound of the formula (c) | 1.35 | 0.39 | 0.09 |
| | other impurity | — | 2.72 | 0.55 |

From the HPLC analysis results, the compounds of the formulas (d)-(j) were not detected in the obtained crystal of 2-naphthylacetonitrile.

Example 5

In the same manner as in Example 4 except that the time for dropwise addition of reaction starting material 1 was changed from 1 hr to 8 min, the reaction was performed.

The reaction mixture obtained by reacting reaction starting material 1 and reaction starting material 2 for 4 hr was measured by HPLC. As a result, 2-naphthylacetonitrile (95.94 area %) and the compound of the formula (c) (0.30 area %) were contained.

Example 6

In the same manner as in Example 4 except that the time for dropwise addition of reaction starting material 1 was changed from 1 hr to 4 hr, the reaction was performed.

The reaction mixture obtained by reacting reaction starting material 1 and reaction starting material 2 for 4 hr was measured by HPLC. As a result, 2-naphthylacetonitrile (96.37 area %) and the compound of the formula (c) (0.70 area %) were contained.

Comparative Example 1

In the same manner as in Example 4 except that the time for dropwise addition of reaction starting material 1 was changed from 1 hr to 10 hr, 2-naphthylacetonitrile was synthesized.

The reaction mixture obtained by reacting reaction starting material 1 and reaction starting material 2 for 4 hr was measured by HPLC. As a result, 2-naphthylacetonitrile (92.75 area %) and the compound of the formula (c) (1.16 area %) were contained.

The obtained 2-naphthylacetonitrile was analyzed by HPLC. As a result, the content of 2-naphthylacetonitrile was 97.44 area %, and the content of the compound of the formula (c) was 0.47 area %.

The dropwise addition time and the addition amount of reaction starting material 1, and the contents of the 2-naphthylacetonitrile and the compound of the formula (c) in the reaction mixture obtained by reacting for 4 hr are shown in Table 7.

In Table 7, the addition amount of reaction starting material 1 means the addition amount (mol/min) of the acid chloride compound contained in reaction starting material 1 per 1 mol of sulfamide contained in the reaction starting material 2.

TABLE 7

| | reaction starting material 1 | | content in the reaction mixture (area %) | |
|---|---|---|---|---|
| | dropwise addition time | addition amount (mol/min) | 2-naphthyl-acetonitrile | compound of formula (c) |
| Example 4 | 1 hr | 0.014 | 96.27 | 0.39 |
| Example 5 | 8 min | 0.104 | 95.94 | 0.30 |
| Example 6 | 4 hr | 0.0035 | 96.37 | 0.70 |
| Comparative Example 1 | 10 hr | 0.0014 | 92.75 | 1.16 |

As is clear from Table 7, a smaller amount of the compound of the formula (c) is produced when the addition amount (mol/min) of the acid chloride compound contained in the reaction starting material 1 is larger.

However, when the addition amount (mol/min) of the acid chloride compound contained in the reaction starting material 1 is too large, a large amount of hydrochloric acid gas as a by-product may be generated. It is thus necessary to pay attention to safety by, for example, providing a processing apparatus and the like in the case of industrial production of a large amount.

INDUSTRIAL APPLICABILITY

According to the present invention, high purity 2-naphthylacetonitrile with less impurity which is useful as a starting material or intermediate for the synthesis of various pharmaceutical products, agricultural chemicals, and chemical products, particularly a starting material or intermediate for the synthesis of pharmaceutical products, can be provided. In addition, a production method capable of producing high purity 2-naphthylacetonitrile safely, highly efficiently, industrially in a large amount at a low cost can be provided. Furthermore, using the 2-naphthylacetonitrile of the present invention, pharmaceutical products such as (1R, 5S)-1-(naphthalen-2-yl)-3-azabicyclo[3.1.0]hexane and the like can be produced industrially in a large amount at a low cost.

This application is based on a patent application No. 2019-196782 filed in Japan (filing date: Oct. 29, 2019), the contents of which are incorporated by reference in full herein.

The invention claimed is:

1. A method for producing a high purity 2-naphthylacetonitrile, the method comprising reacting 2-naphthylacetic acid and a halogenating agent, mixing a first reaction starting material comprising an obtained acid halide compound of formula (5), in which X is a halogen atom,

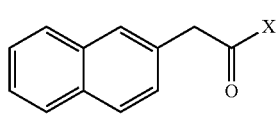

(5)

and a second reaction starting material comprising sulfamide at a temperature of from 10° C. to 100° C., and
raising the temperature to from 85° C. to 120° C. to give 2-naphthylacetonitrile.

2. The method according to claim 1, wherein the first reaction starting material is added to the second reaction starting material at a temperature of from 10° C. to 100° C., and the temperature is raised to a temperature of from 85° C. to 120° C. to give 2-naphthylacetonitrile.

3. The method according to claim 1, wherein the first reaction starting material is added to the second reaction starting material such that an amount of the acid halide compound is not less than 0.0027 mol/min per 1 mol of the sulfamide.

4. The method according to claim 1, wherein an amount of the sulfamide is 1 mol to 5 mol per 1 mol of the 2-naphthylacetic acid.

5. The method according to claim 2, wherein an amount of the sulfamide is 1 mol to 5 mol per 1 mol of the 2-naphthylacetic acid.

6. The method according to claim 2, wherein the first reaction starting material is added to the second reaction starting material such that an amount of the acid halide compound is not less than 0.0027 mol/min per 1 mol of the sulfamide.

7. The method according to claim 4, wherein the first reaction starting material is added to the second reaction starting material such that an amount of the acid halide compound is not less than 0.0027 mol/min per 1 mol of the sulfamide.

8. A method for producing high purity 2-naphthylacetonitrile, the method comprising:
  subjecting 2'-acetonaphthone to a Willgerodt reaction, optionally in the presence of an additive, to obtain an amide compound;
  hydrolyzing the amide compound; and
  liberating 2-naphthylacetic acid to give 2-naphthylacetic acid;
  mixing a first reaction starting material comprising the liberated 2-naphthylacetic acid, a halogenating agent, and a first organic solvent, and a second reaction starting material comprising sulfamide and a second organic solvent at a temperature in a range of from 10° C. to 100° C.; and
  raising the temperature to a range of from 85° C. to 120° C. to give 2-naphthylacetonitrile.

* * * * *